(12) United States Patent
Takahashi et al.

(10) Patent No.: US 8,680,484 B2
(45) Date of Patent: Mar. 25, 2014

(54) FLUORESCENCE ANALYZING APPARATUS AND FLUORESCENCE DETECTING APPARATUS

(75) Inventors: Satoshi Takahashi, Hitachinaka (JP); Tsuyoshi Sonehara, Kokubunji (JP); Takanobu Haga, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 34 days.

(21) Appl. No.: 13/380,251

(22) PCT Filed: Jun. 4, 2010

(86) PCT No.: PCT/JP2010/003729
§ 371 (c)(1),
(2), (4) Date: Dec. 22, 2011

(87) PCT Pub. No.: WO2010/150468
PCT Pub. Date: Dec. 29, 2010

(65) Prior Publication Data
US 2012/0097864 A1   Apr. 26, 2012

(30) Foreign Application Priority Data

Jun. 25, 2009 (JP) .................. 2009-150445
Nov. 27, 2009 (JP) .................. 2009-269404

(51) Int. Cl.
*G01N 21/64* (2006.01)

(52) U.S. Cl.
USPC ..................................... 250/458.1

(58) Field of Classification Search
USPC ..................................... 250/458.1
See application file for complete search history.

(56) References Cited

U.S. PATENT DOCUMENTS

| 5,332,905 | A  | * | 7/1994 | Brooker et al. ............ 250/458.1 |
| 6,262,837 | B1 |   | 7/2001 | Nagano et al. |
| 6,747,281 | B2 | * | 6/2004 | Sendai et al. ............. 250/458.1 |

(Continued)

FOREIGN PATENT DOCUMENTS

| JP | 4-315119 | 11/1992 |
| JP | 9-257813 | 10/1997 |

(Continued)

OTHER PUBLICATIONS

Takashi Funatsu et al., Imaging of Single fluorescent molecules and individual ATP molecules in aqueous solution, Letter to Nature, Apr. 6, 1995, pp. 555-559, vol. 374.

(Continued)

*Primary Examiner* — Kiho Kim
(74) *Attorney, Agent, or Firm* — Antonelli, Terry, Stout & Kraus, LLP.

(57) ABSTRACT

Provided are a method and an apparatus for easily identifying and detecting fluorescent material types captured in respective reaction regions of a substrate, particularly, a method and an apparatus for identifying and measuring the fluorescence intensities of a plurality of fluorescent materials using a small pixel count. The fluorescence intensities of four or more types of fluorescent materials are divided by a dividing section at ratios different at least for each fluorescence maximum wavelength range, and are detected by at least one detector including pixels for detecting the light fluxes divided at the different ratios. The type of the fluorescent material is determined on the basis of the ratio of the detected fluorescence intensity of the same detection portion, and the fluorescence intensity is measured.

19 Claims, 27 Drawing Sheets

(56) References Cited

U.S. PATENT DOCUMENTS

| | | |
|---|---|---|
| 6,917,726 B2 | 7/2005 | Levene et al. |
| 7,136,161 B2 | 11/2006 | Nakamura |
| 7,148,492 B2 * | 12/2006 | Loney et al. ............... 250/458.1 |
| 2005/0225764 A1 * | 10/2005 | Bacarese-Hamilton et al. .......................... 356/417 |
| 2007/0281315 A1 | 12/2007 | Takahashi et al. |
| 2008/0174776 A1 * | 7/2008 | Inoue et al. ................... 356/317 |
| 2008/0241843 A1 * | 10/2008 | Zare et al. ......................... 435/6 |
| 2009/0079988 A1 | 3/2009 | Narahara et al. |
| 2009/0242798 A1 * | 10/2009 | Bewersdorf et al. ....... 250/458.1 |

FOREIGN PATENT DOCUMENTS

| | | |
|---|---|---|
| JP | 2000-98244 | 4/2000 |
| JP | 2005-70031 | 3/2005 |
| JP | 2004-341204 | 12/2007 |
| JP | 2007-322185 | 12/2007 |
| JP | 2009-74947 | 4/2009 |
| JP | 2009-122203 | 6/2009 |

OTHER PUBLICATIONS

Ido Braslavsky et al., Sequence information can be obtained from single DNA molecules, PNAS, Apr. 1, 2003, pp. 3960-3964, vol. 100, No. 7.

M. J. Levene et al., Zero-Mode Waveguides for Single-Molecule Analysis at High Concentrations, Science, Jan. 31, 2003, pp. 682-686, vol. 299.

Hameer Ruparel, et al., Design and synthesis of a 3'-$O$-allyl photocleavable fluorescent nucleotide as a reversible terminator for DNA sequencing by synthesis, PNAS, Apr. 26, 2005, pp. 5932-5937, vol. 102, No. 17.

Office Action Dated Apr. 16, 2013, issued in corresponding Japanese Patent Application No. 2009-269404.

* cited by examiner

Fig. 2
(A)
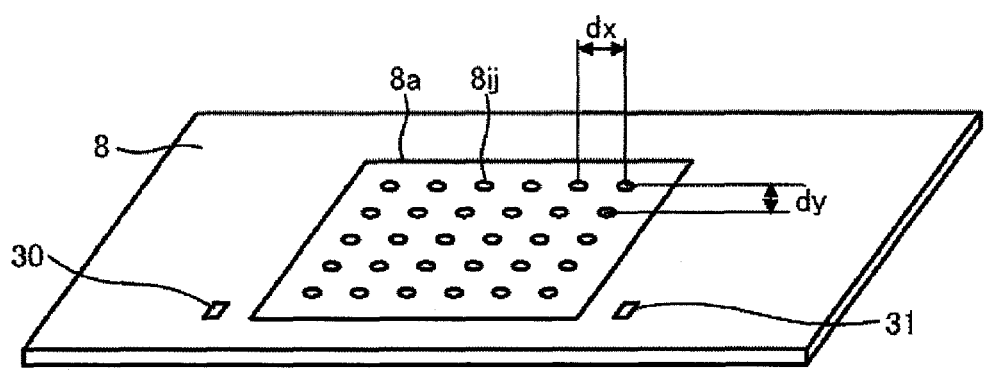
(B)
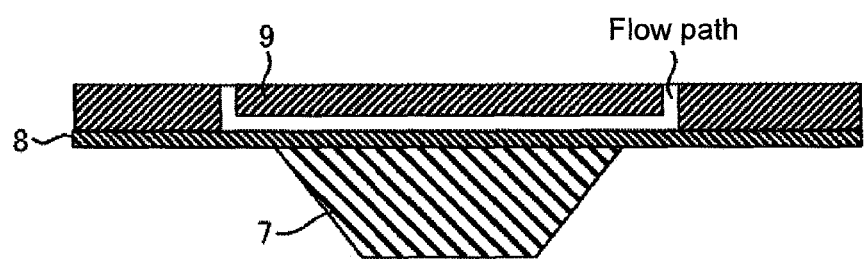

Fig. 4
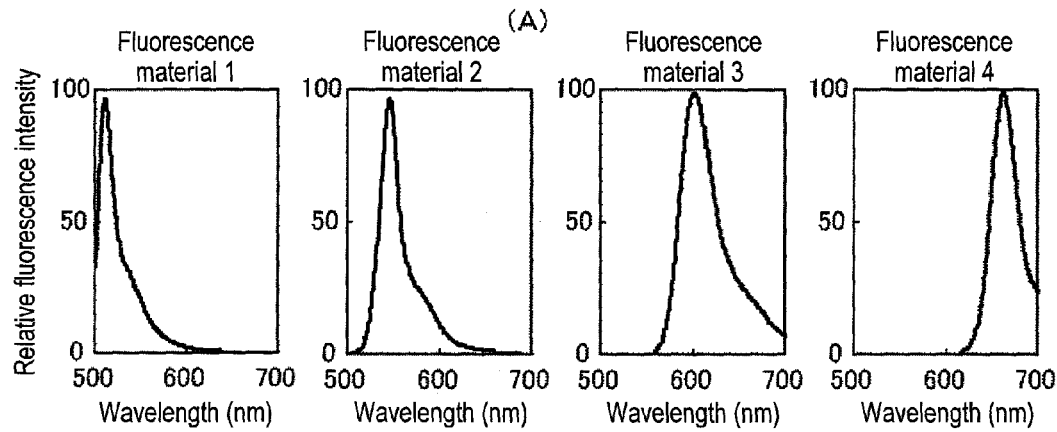
Fluorescence spectra of four types of fluorescent materials
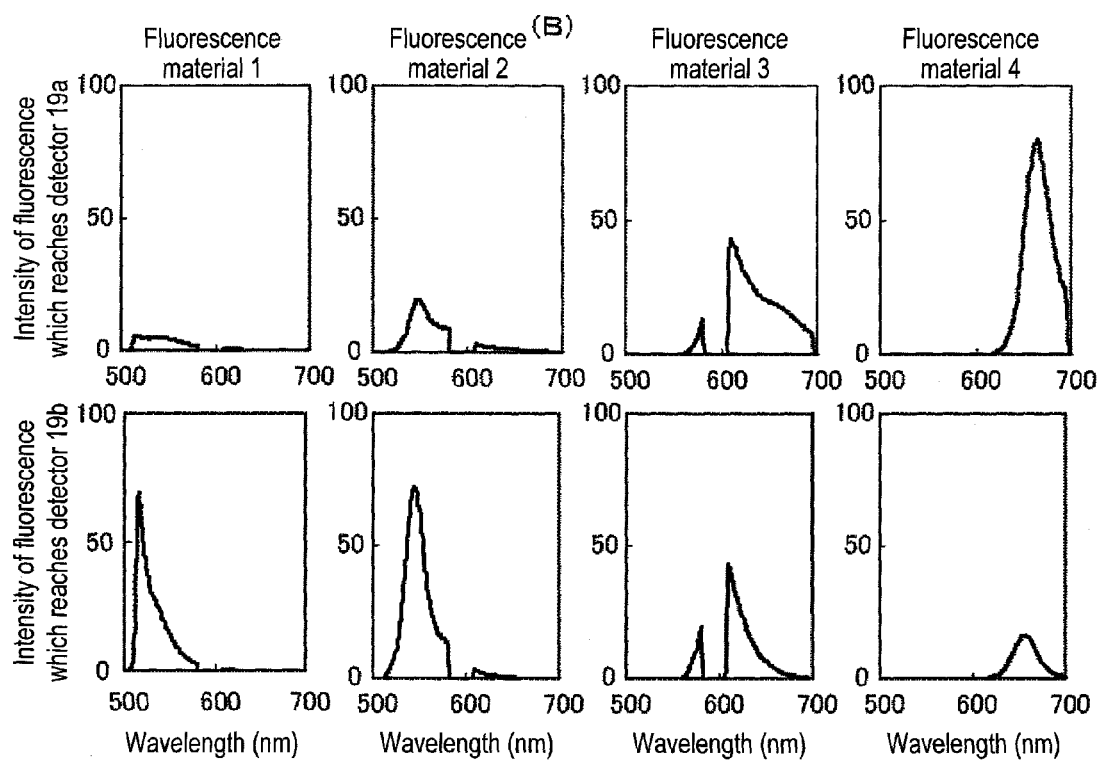
Spectral characteristics of light fluxes which reach detectors after passing through filters and mirrors

| Fluorescence material type | | Fluorescence material 1 | Fluorescence material 2 | Fluorescence material 3 | Fluorescence material 4 |
|---|---|---|---|---|---|
| Detected light intensity when corresponding fluorescence material is detected | Detector 19a | 15 | 25 | 63 | 84 |
| | Detector 19b | 85 | 75 | 37 | 16 |

Fig. 15
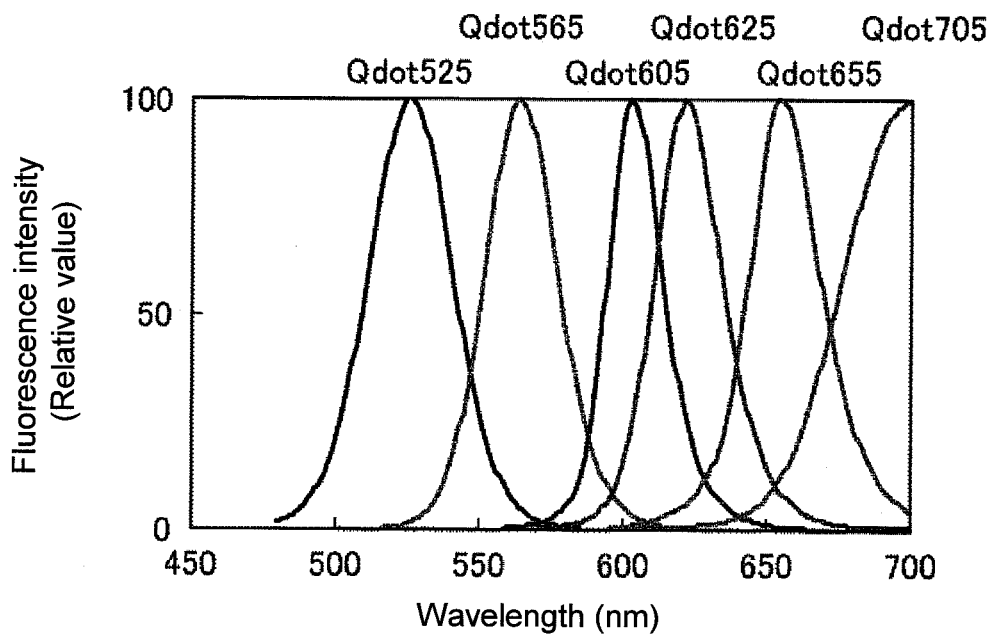
(A)
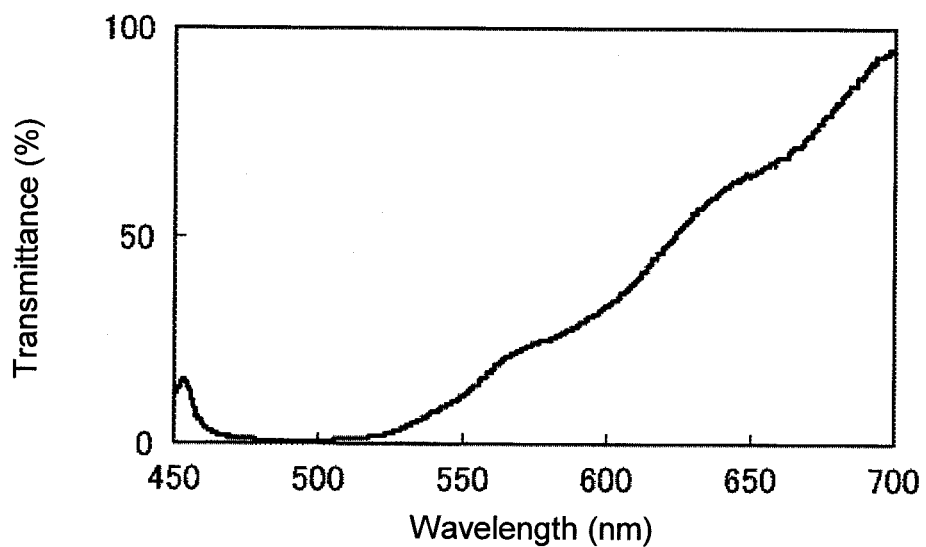
(B)

Fluorescent images of the same bright spot

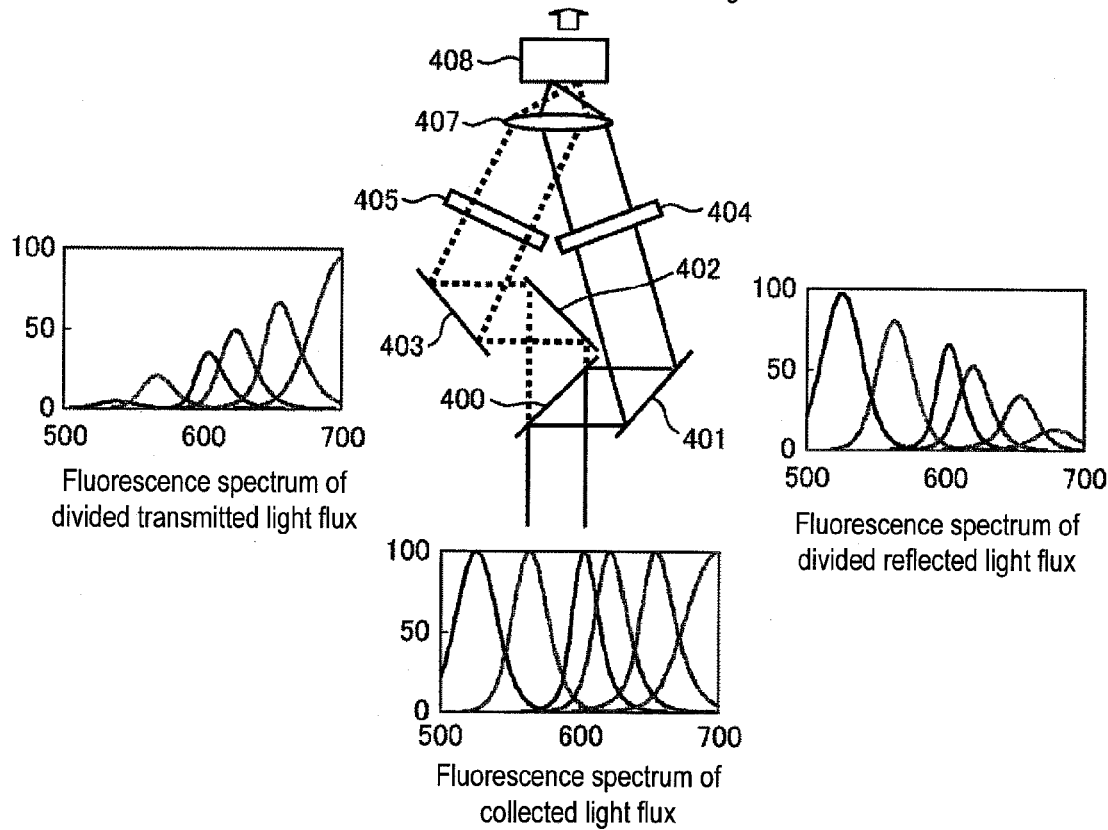

Schematic view of detected images

Fluorescence spectrum of divided transmitted light flux

Fluorescence spectrum of divided reflected light flux

Fluorescence spectrum of collected light flux (B)

Fluorescent images of the same bright spot

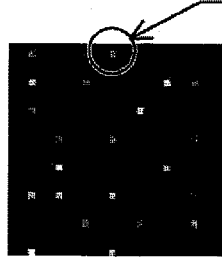 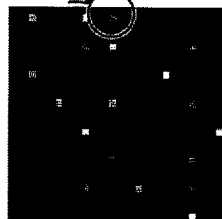

Part of divided transmitted light image   Part of divided reflected light image

Fig. 17
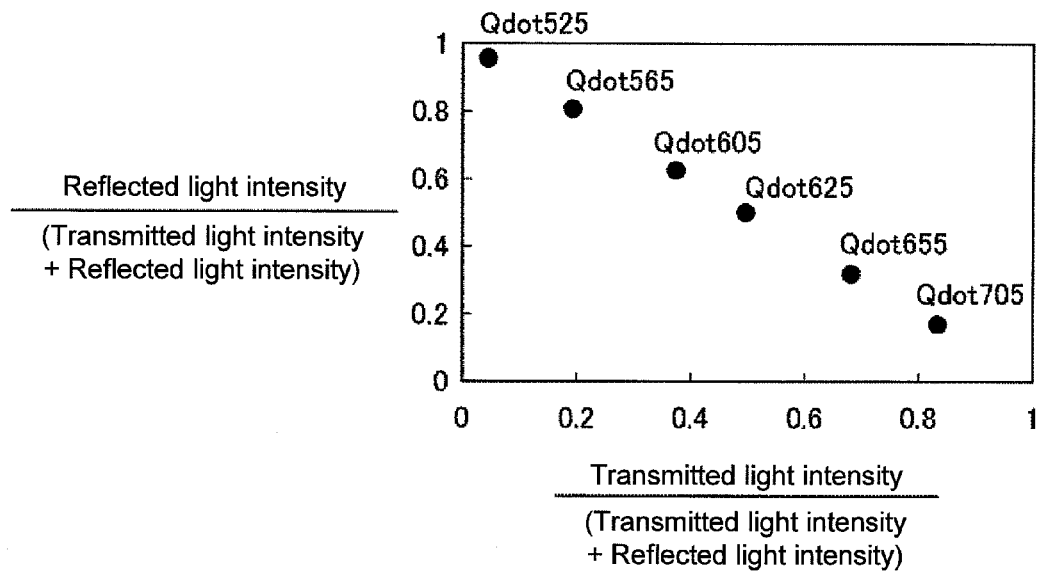
Fig. 18
(A)
Fluorescent images of the same bright spot
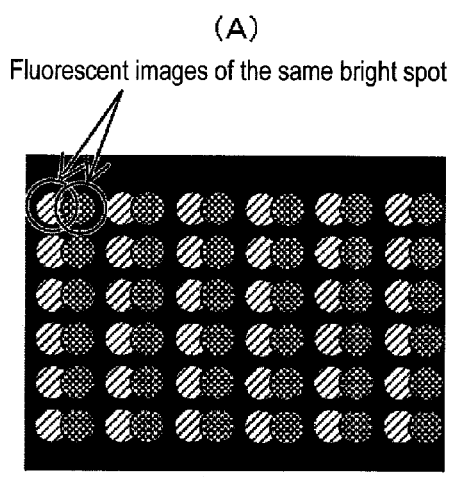
(B)
Fluorescent images of the same bright spot
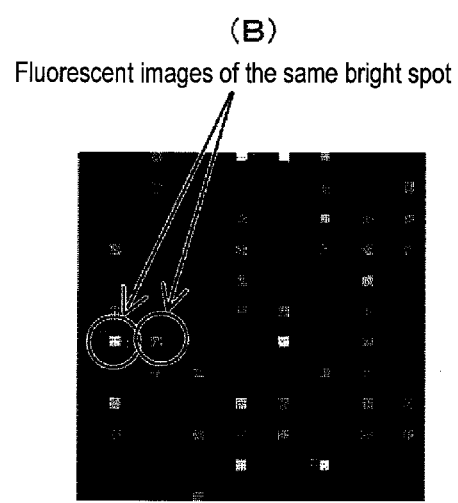
Part of simultaneously measured image example of divided transmitted light image and divided reflected light image

Fig. 24
(A)
Acceptor fluorescent images of the same bright spot A
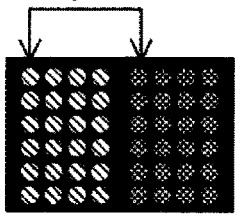
Schematic view of detected images
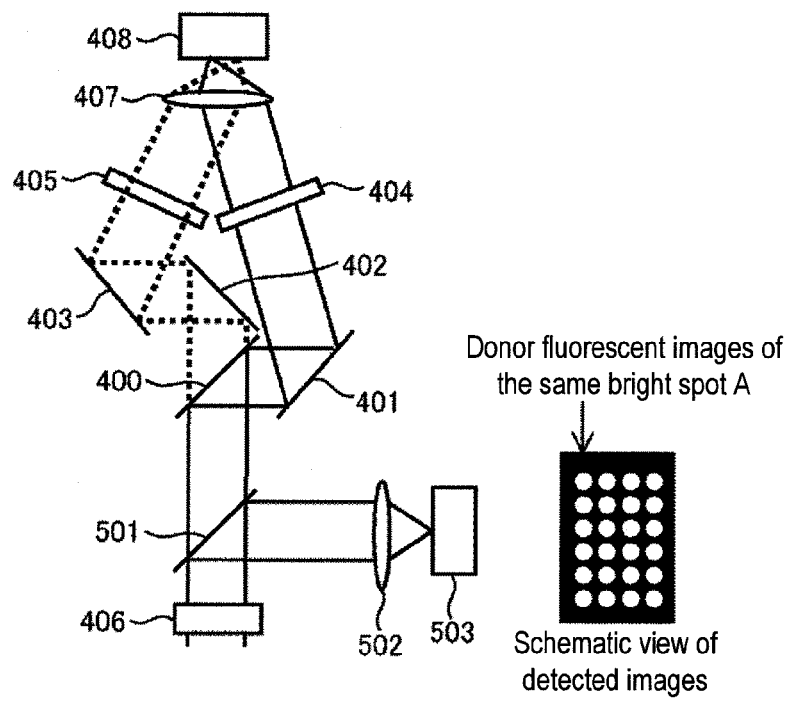
Donor fluorescent images of the same bright spot A
Schematic view of detected images
(B)
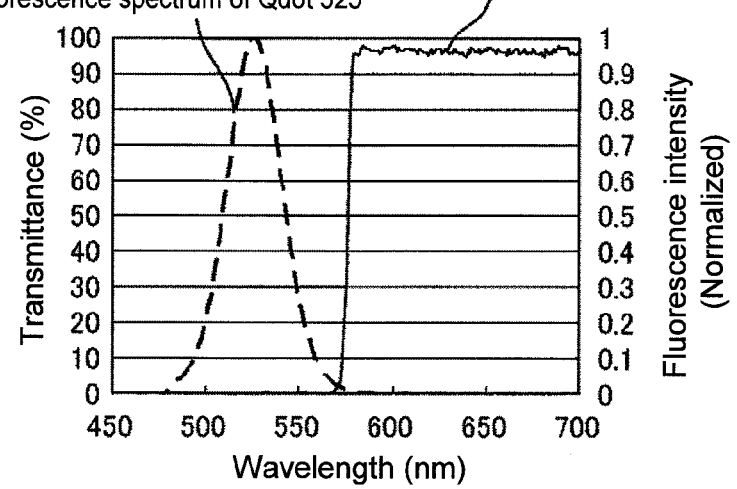

Fig. 26
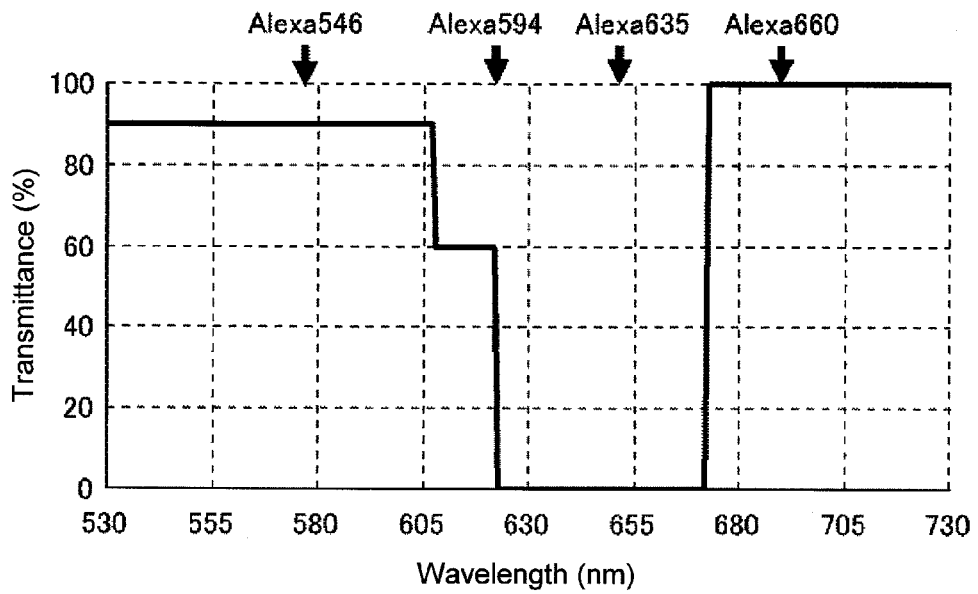
(A)
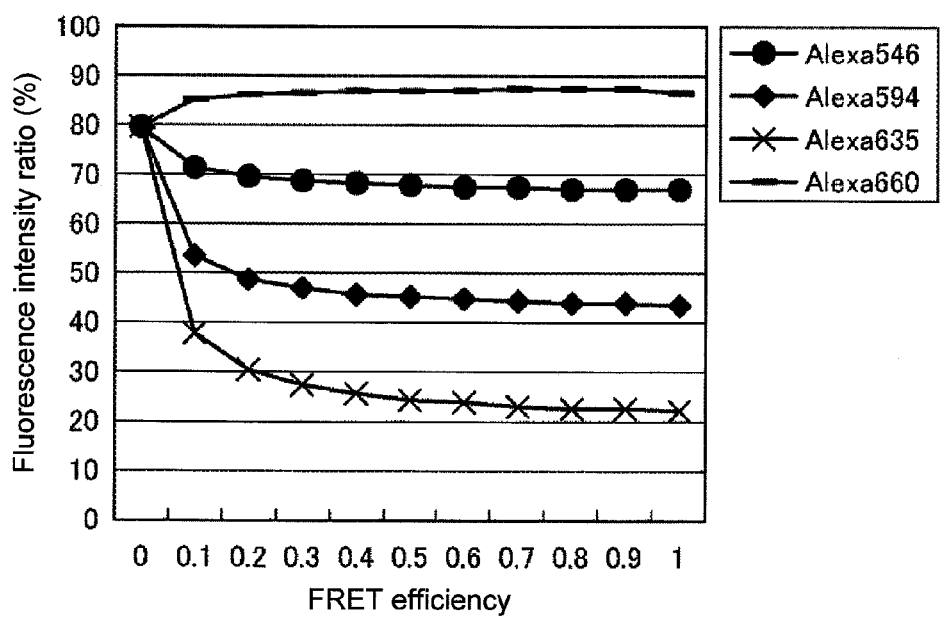
(B)
(C)
| Fluorescence material type | Alexa546 | Alexa594 | Alexa635 | Alexa660 |
|---|---|---|---|---|
| Fluorescence intensity ratio | 68% | 45% | 24% | 87% |

Fig. 27
Fluorescent images of the same bright spot
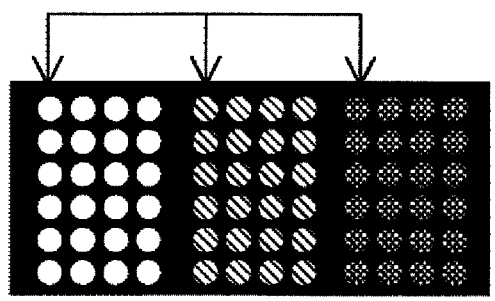
Schematic view of detected images
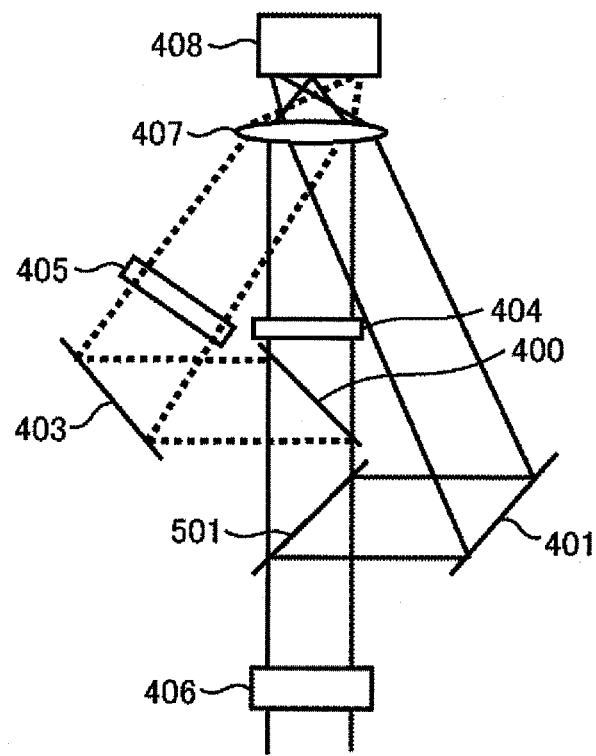

Fig. 28
(A)
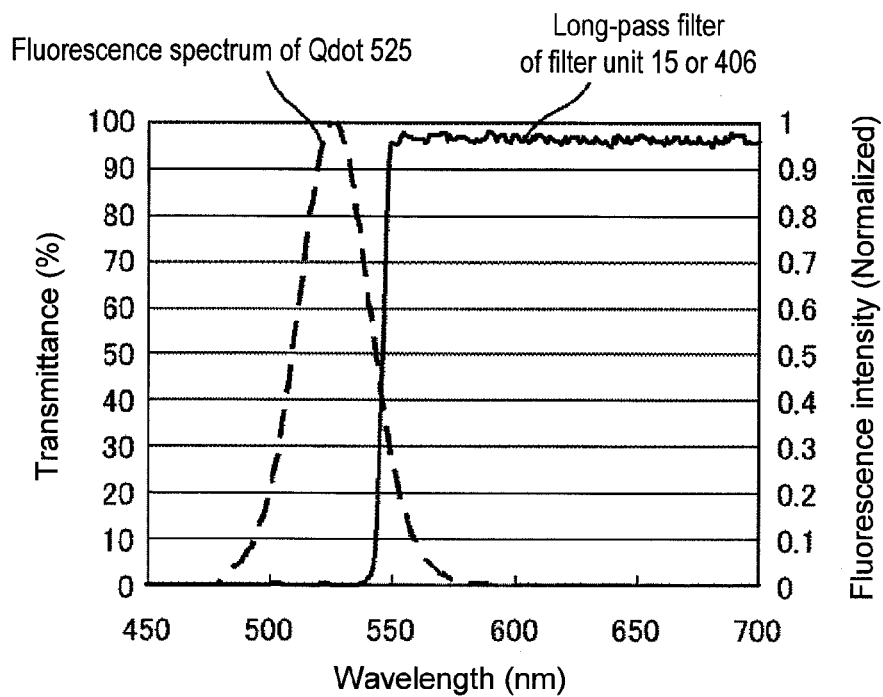
(B)
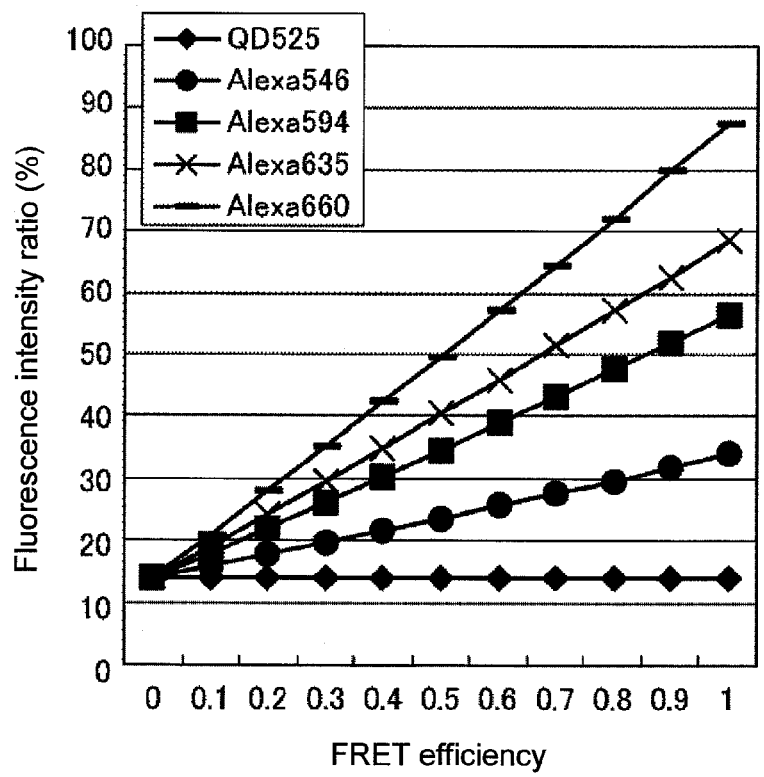

Fig. 29
(A)
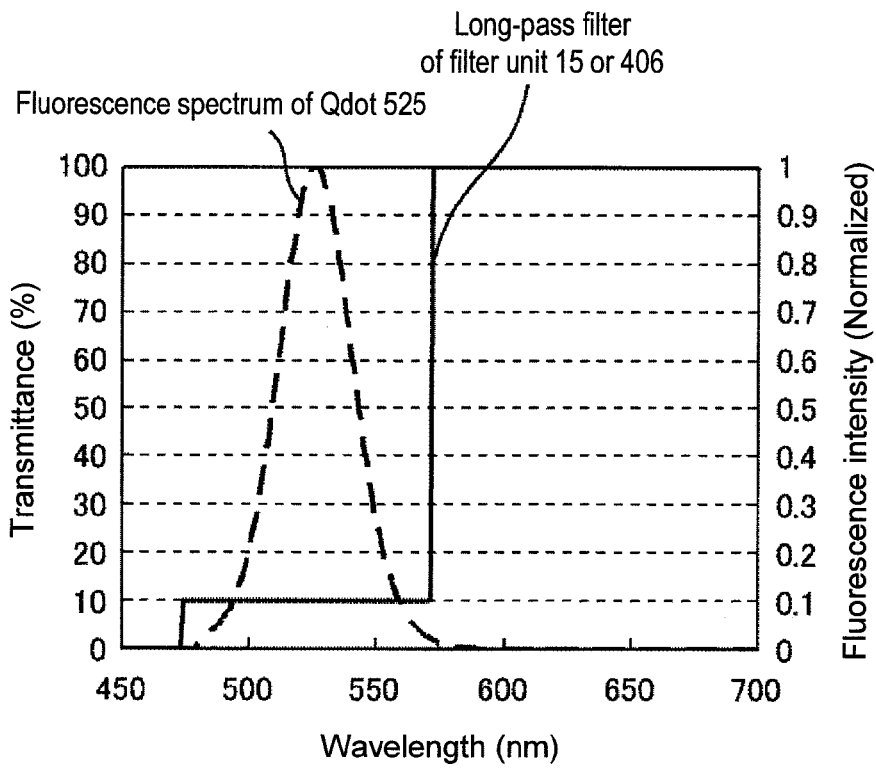
(B)
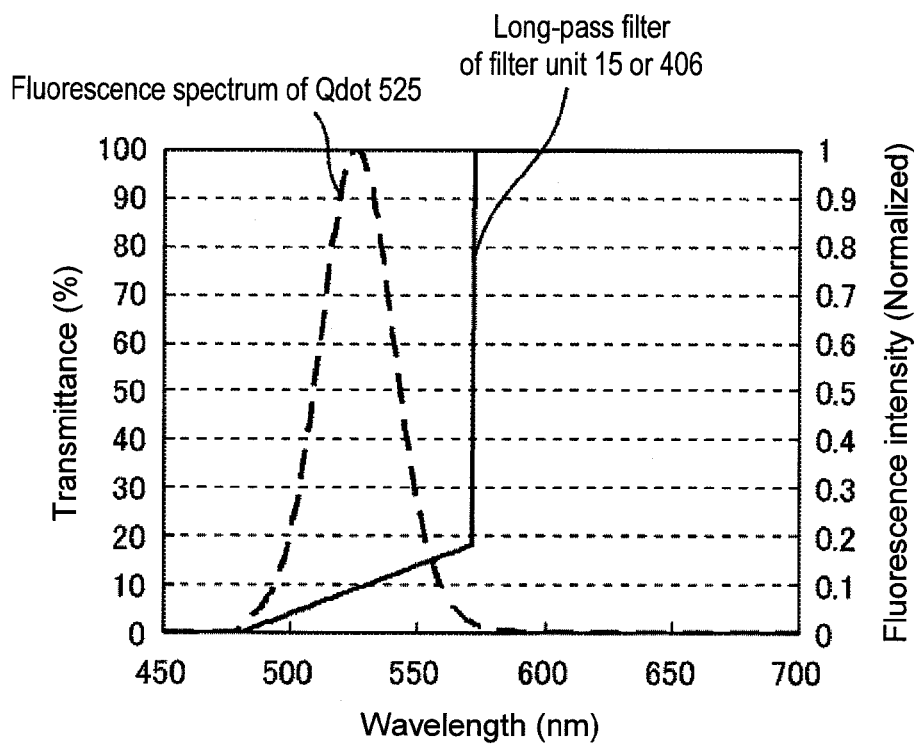

Fig. 31
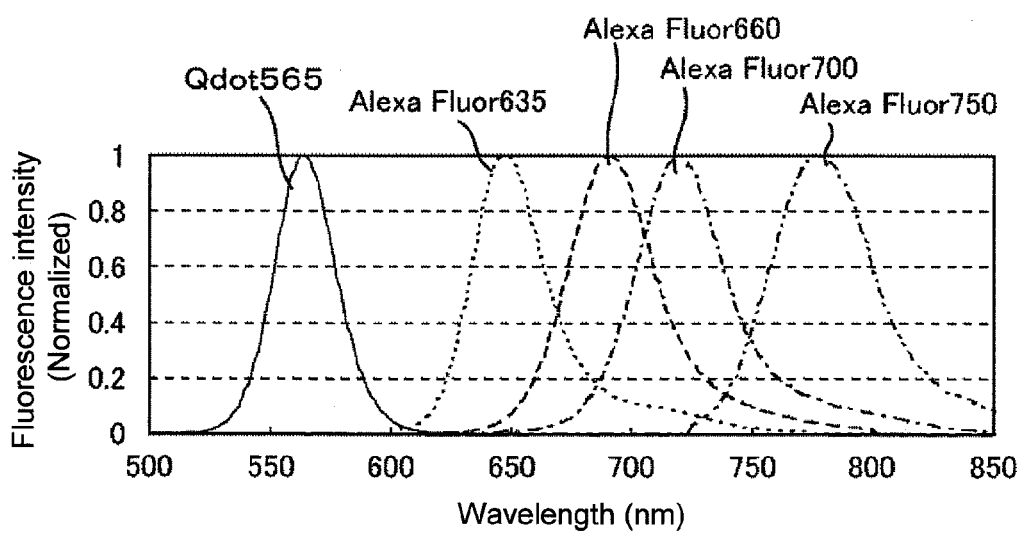
(A)
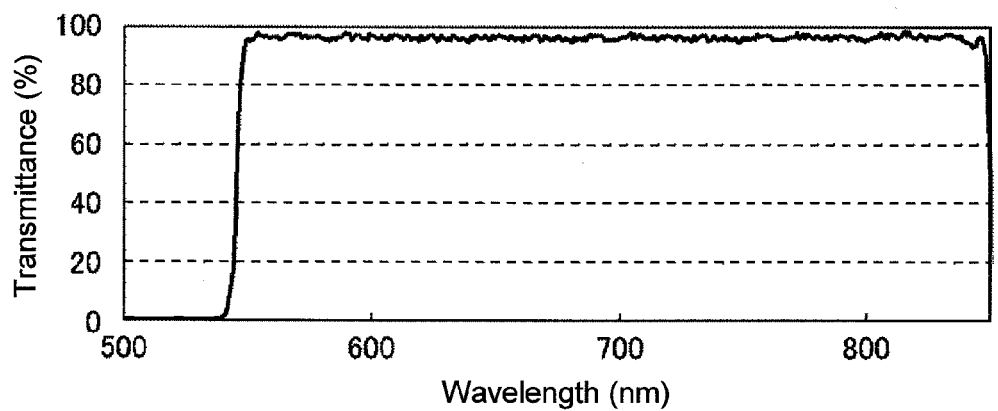
(B)
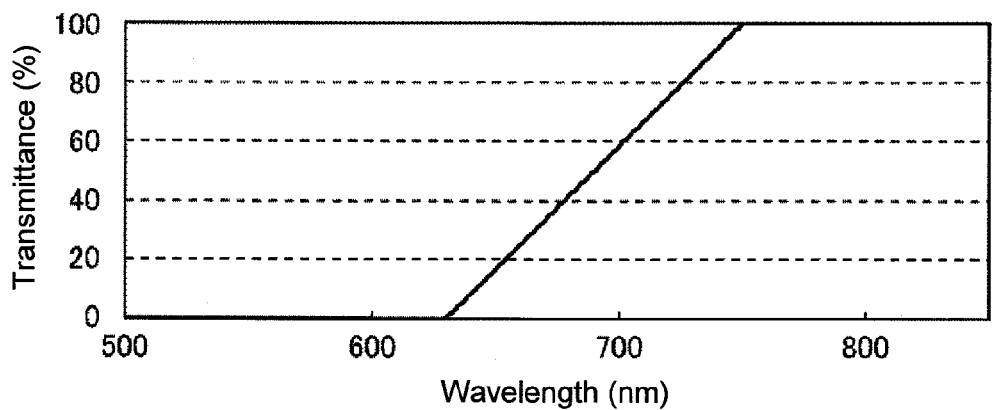
(C)

FLUORESCENCE ANALYZING APPARATUS AND FLUORESCENCE DETECTING APPARATUS

TECHNICAL FIELD

The present invention relates to a light analyzing apparatus, for example, a light measuring/analyzing apparatus which irradiates light to DNA, RNA, or biologically relevant substances such as proteins and cells to perform light analysis.

BACKGROUND ART

Up to now, there has been proposed a method of radiating excitation light to an object disposed on a surface of a substrate to observe the shape of the object. For example, Patent Literature 1 describes an apparatus which radiates excitation light outputted from an excitation light source to a transparent substrate, causes total reflection of the excitation light inside of the transparent substrate to thereby generate an evanescent wave on a substrate surface, and detects scattered light of the evanescent wave due to a sample on the substrate. Note that the apparatus described in Patent Literature 1 does not disperse the scattered light.

In addition, for example, Patent Literature 2 describes an apparatus which disperses fluorescence and scattered light deriving from sample components excited by an evanescent wave. Note that, in the apparatus described in Patent Literature 2, the sample components are not captured on a flow path boundary plane.

Meanwhile, there has been proposed an apparatus which captures a plurality of biological molecules on a substrate surface, generates an evanescent wave in a given range of the substrate surface similarly to Patent Literature 1, and creates an image of light emitted from the biological molecules excited by the evanescent wave. Nonfluorescent biological molecules are captured on the substrate, a reaction liquid containing fluorescent molecules is fed onto the substrate, and fluorescence from a capture position of the biological molecules is observed. This enables observation of a binding reaction between the biological molecules and the molecules contained in the reaction liquid. For example, first, unmodified single-stranded DNA is captured on the substrate, a reaction liquid containing fluorescently-modified bases modified with fluorescent materials different for each base type is introduced, and fluorescence from a molecule capture position is dispersed while complementary bases are bound to the single-stranded DNA, whereby the sequence of the captured DNA can be decoded.

In recent years, as described in Non Patent Literature 2, it has been proposed to capture DNA and the like on a substrate and determine a nucleotide sequence thereof. Sample DNA fragments to be analyzed are randomly captured molecule by molecule on the substrate surface to be elongated substantially for each base, and results thereof are detected by fluorescence measurement, whereby a nucleotide sequence thereof is determined. Specifically, in one cycle, performed are: a step of causing a DNA polymerase reaction using four types of dNTP derivatives (MdNTPs) which can be each taken into a template DNA as a substrate of a DNA polymerase to stop a DNA chain elongation reaction by the presence of a protecting group, the dNTP derivatives each having a detectable label; then, a step of detecting the taken-in MdNTPs by fluorescence detection or the like; and a step of bringing the MdNTPs back into an elongatable state. Such a cycle of the steps is repeated to determine the nucleotide sequence of the sample DNA. According to this technique, because the sequences of the DNA fragments can be determined molecule by molecule, a large number of fragments can be analyzed at the same time, leading to enhancement in analysis throughput. In addition, according to this technique, because there is a possibility that the nucleotide sequence can be determined for each single DNA molecule, the need for purification and amplification of a sample DNA in cloning or PCR, which has been a problem in conventional techniques, may be eliminated, and an increase in speed of genomic analysis and genetic diagnosis can be expected. Note that, according to this technique, because the sample DNA fragment molecules to be analyzed are randomly captured on the substrate surface, an expensive camera having a pixel count of several hundred times the number of the captured DNA fragment molecules is necessary. That is, in the case where an interval between the DNA fragment molecules is adjusted to 1 micrometer on average, an interval between some molecules is larger, and an interval between other molecules is smaller. Hence, in order to detect such molecules separately from one another, it is necessary to detect a fluorescent image at a smaller interval in terms of the substrate surface. In general, measurement at an interval of about one tenth is necessary.

Meanwhile, in Non Patent Literature 3 and Patent Literature 3, the sensitivity of fluorescence detection is further enhanced according to a nano-aperture evanescent radiation/detection method which can further reduce the radiation volume of excitation light than the total-reflection evanescent radiation/detection method. Two glass substrates, that is, a glass substrate A and a glass substrate B are disposed parallel to each other, and a planar aluminum thin film, which includes a nano-aperture having a diameter of 50 nm and has a film thickness of about 100 nm, is laminated on a surface of the glass substrate A, the surface facing the glass substrate B. The aluminum thin film needs to have a light-blocking property. A reaction vessel is formed between the two glass substrates, and the reaction vessel is filled with a solution, whereby a solution layer is formed between the two glass substrates. The reaction vessel is provided with an inlet and an outlet for the solution. The solution is fed from the inlet, and the solution is discharged from the outlet, whereby the solution can be flowed in a direction parallel to the glass substrates and the aluminum thin film. This enables the solution in the solution layer to have given compositions. If excitation light which is oscillated from an Ar ion laser and has a wavelength of 488 nm is radiated perpendicularly to the glass substrate A from the opposite side to the glass substrate B while being focused by an objective lens, an evanescent field of the excitation light is formed in a portion of the solution layer near a bottom plane inside of the nano-aperture, and the excitation light does not further propagate outside of the portion of the solution layer. Meanwhile, fluorescence emission is detected by forming an image thereof on a two-dimensional CCD using the objective lens. In the evanescent field, the excitation light intensity exponentially decreases with increasing distance from the nano-aperture bottom plane, and the excitation light intensity is $1/10$ at a distance of approximately 30 nm from the nano-aperture bottom plane. Further, according to the nano-aperture evanescent radiation/detection method, the radiation width of excitation light in the direction parallel to the glass substrates is limited to the aperture diameter, that is, 50 nm, unlike the total-reflection evanescent radiation/detection method, and hence the radiation volume of excitation light is further reduced. For this reason, background light caused by, for example, fluorescence emission of free fluorescent materials and Raman scattering of water can be dramatically reduced. As a result, only fluorescent materials labeled to target biological molecules can be selectively detected in the presence of higher-concentration free fluorescent materials, so that extremely high-sensitive fluorescence detection can be achieved. In these literatures, such a fluorescence detection method as described above is applied to take-in measurement of dNTPs using an elongation reaction of DNA molecules.

CITATION LIST

Patent Literature

Patent Literature 1: JP Patent Publication (Kokai) No. 09-257813 A (1997)
Patent Literature 2: JP Patent Publication (Kokai) No. 2005-70031 A
Patent Literature 3: U.S. Pat. No. 6,917,726

Non Patent Literature

Non Patent Literature 1: Nature Vol. 374, 555-559 (1995)
Non Patent Literature 2: Proc. Natl. Acad. Sci. USA, vol. 100, pp. 3960, 2003
Non Patent Literature 3: SCIENCE 2003, Vol. 299, pp. 682-686
Non Patent Literature 4: Proc. Natl. Acad. Sci. USA, vol. 102, pp. 5932, 2005

SUMMARY OF INVENTION

Technical Problem

In the apparatus which creates an image of fluorescence of biological molecules captured on a substrate surface to thereby analyze the biological molecules, in general, different types of biological molecules are captured for each capture region (spot) on the substrate, an image of fluorescence from each spot is created for separation, and the fluorescence is detected. In order to analyze many types of biological molecules in the shortest time possible and reduce the amount of consumed reagent, it is preferable that the spots for capturing the biological molecules be defined on the substrate at the highest density possible in an optically resolvable range. In addition, in order to reduce the amount of reagent consumed for each spot, the smaller number of biological molecules captured at one spot is more advantageous, and one molecule is ideal. As described in Non Patent Literature 1, the fluorescence detection method has such a sensitivity that enables detection of even one molecule, but a spectroscopic imaging method, which causes a small loss, is preferable in order to disperse and detect fluorescence from a small number of molecules to obtain an excellent S/N ratio. Accordingly, it is preferable to adopt: a dispersive spectroscopic imaging method using a dispersive element such as a prism or diffraction grating; or a method of dispersing light using a dichroic mirror to obtain an image using a plurality of image sensors (dichroic mirror/multi-sensor spectroscopic imaging method). In addition, in the case where light emissions from fluorescent materials do not occur at the same time or do not need to be measured at the same time, transmission filters dedicated to the fluorescent materials may be used, and one filter may be sequentially replaced with another to repeat light measurement, as described in Non Patent Literature 2.

As described above, it is preferable to define the plurality of spots on the substrate at the highest density possible in an optically resolvable range, but according to the dichroic mirror/multi-sensor spectroscopic imaging method, a number of image sensors are necessary, the number corresponding to the number of types of fluorescently-labeled objects to be used, and this leads to an increase in costs of a detecting apparatus. In addition, a fluorescent image is divided by a normal dichroic mirror or the like, and hence the S/N ratio is not necessarily high in many cases. In the case where the spectral filters are sequentially replaced with one another for light measurement, the number of necessary image sensors can be one, but a mechanism for replacing the filters is necessary, resulting in a higher possibility of mechanical failure as well as an increase in apparatus costs. In addition, because the time required to replace the filters is relatively long, a change in fluorescence based on a rapid reaction cannot be dealt with, and because one wavelength range can be measured at the same time, light fluxes having different fluorescence wavelengths cannot be detected at the same time. The dispersive spectroscopic imaging method has the advantage that detection can be achieved using the smallest number (for example, one) of image sensors, but if an interval between the spots is smaller, a fluorescent image obtained when the wavelength of fluorescence emitted from one spot is dispersed overlaps with a fluorescent image of another spot adjacent thereto, resulting in a decrease in fluorescence identification accuracy. For this reason, in order to enhance the fluorescence detection accuracy, it is necessary to increase an interval between the spots on the substrate at which the biological molecules are captured, leading to difficulty in achieving higher density.

In addition, in conventional optical systems, in the case where the biological molecules are randomly captured on the substrate, a pixel count of several hundred or more times the number of spots on the substrate is necessary. As a result, the detection speed is lower, and an expensive two-dimensional sensor is necessary. Moreover, a fluorescent image needs to be detected at higher resolution, and hence it is necessary to use a light collecting lens having a large numerical aperture NA, resulting in an expensive system.

An object of the present invention relates to an apparatus which identifies and measures the fluorescence intensities of a plurality of fluorescent materials using a small pixel count. Further, an object of the present invention relates to providing a detection method at low cost or with high operability, for example, when a fluorescent image of a DNA fragment molecule captured on a substrate is subjected to fluorescence detection by a two-dimensional sensor.

Solution to Problem

The present invention provides an apparatus which irradiates light for fluorescence measurement to a substrate on which biologically relevant molecules such as oligonucleotides are captured, collects fluorescence generated therefrom, forms an image of the collected fluorescence on a two-dimensional detector, and causes the two-dimensional detector to perform fluorescence detection, the apparatus including: a substrate including a plurality of regions in which biologically relevant molecules are to be captured, the molecules being individually or simultaneously labeled with a plurality of types of fluorescent materials, dyes, or the like so as to be detectable; a light source for light excitation; a radiation optical system; a fluorescence collecting system; a dividing section which divides collected light at ratios substantially different for each specified wavelength; a detector including a plurality of pixels for detecting each divided light flux; and a data processing section which computes fluorescence intensity ratios of corresponding divided image positions, and identifies the plurality of types of fluorescent materials on a basis of the fluorescence intensity ratios.

Advantageous Effects of Invention

According to the present invention, when a fluorescent image of a sample on a substrate is measured, the fluorescence intensities of a plurality of fluorescent materials can be calculated using a smaller number of detectors than the number of types of the fluorescent materials, whereas the same number of detectors as the number of types thereof has conventionally been required, so that efficient detection can be achieved. In particular, three, four, or more types of fluorescent materials can be identified by one detector, and the fluorescence intensities thereof can be measured, so that a system can be constructed comprehensively at low cost.

In addition, in the case of the dispersive method using a prism or diffraction grating, it is necessary to detect dispersed fluorescence by means of a large number of pixels. Further, in order to prevent one fluorescent image from overlapping with another fluorescent image adjacent thereto, it is necessary to secure a sufficiently large pixel count within a detector, for detecting fluorescence from one capture region. In contrast, according to the present invention, such dispersion is not necessary, and an influence of overlapping with adjacent another portion is small. Accordingly, an interval between regions in which oligonucleotides and the like are captured can be reduced, and fluorescence from a larger number of samples can be analyzed at the same time. The use of such a high-density substrate can lead to enhancement in sample analysis throughput as well as a more simplified system.

In addition, for example, in the case where the number of regions in which oligonucleotides to be measured are captured is the same, efficient detection can be achieved using a smaller pixel count, so that the cost of a two-dimensional sensor can be reduced. In addition, because the optical resolution can be made equivalent to an interval between the regions in which the oligonucleotides are captured, an inexpensive lens can be used instead of a light collecting lens having a large numerical aperture, and an immersion lens does not need to be used, so that the operability can be enhanced.

BRIEF DESCRIPTION OF DRAWINGS

FIG. 1 is a configuration view showing a fluorescence detecting apparatus using a fluorescence analyzing method according to Embodiment 1 of the present invention.

[FIG. 2]FIG. 2 shows structure views each showing a substrate according to Embodiment 1.

FIG. 3 shows characteristic graphs showing filters and a mirror according to Embodiment 1.

[FIG. 4]FIG. 4 shows graphs for describing fluorescence detection of respective fluorescent materials according to Embodiment 1.

FIG. 5 is a table for describing computation results of the fluorescence intensity ratios of the respective fluorescent materials according to Embodiment 1.

FIG. 6 shows another example dichroic mirror according to Embodiment 1 (schematic graph).

FIG. 7 is a configuration view showing a fluorescence detecting apparatus according to Embodiment 2 of the present invention.

FIG. 8 is a configuration view (fluorescence dividing section) showing a fluorescence detecting apparatus according to Embodiment 4 of the present invention.

FIG. 9 shows characteristic graphs (schematic graphs) showing used dichroic mirrors according to Embodiment 4 of the present invention.

FIG. 10 is a structure view showing a joint part between a substrate and a prism for evanescent illumination according to Embodiment 5 of the present invention.

FIG. 11 is a structure view showing the joint part between the substrate and the prism for evanescent illumination according to Embodiment 5 of the present invention.

FIG. 12 is a structure view showing the joint part between the substrate and the prism for evanescent illumination according to Embodiment 5 of the present invention.

FIG. 13 is a structure view showing a substrate according to Embodiment 6 of the present invention.

FIG. 14 is a configuration view showing a fluorescence detecting apparatus according to Embodiment 7 of the present invention.

[FIG. 15]FIG. 15 shows characteristic graphs showing fluorescent materials and a dichroic mirror according to Embodiment 7 of the present invention.

[FIG. 16]FIG. 16 shows schematic views for describing image acquisition by the fluorescence detecting apparatus according to Embodiment 7 of the present invention.

[FIG. 17]FIG. 17 shows example computation results of the fluorescence intensity ratios of respective bright spots according to Embodiment 7 of the present invention.

[FIG. 18]FIG. 18 shows schematic views for describing another image dividing/detecting method according to Embodiment 8 of the present invention.

FIG. 19 shows schematic graphs showing fluorescence intensity measurement and sequence determination of respective bright spots according to Embodiment 9 of the present invention.

FIG. 20(A) shows the wavelengths of lasers for excitation and the excitation spectra of respective fluorescent materials, and FIG. 20(B) is a characteristic graph showing the fluorescence spectra thereof, according to Embodiment 11 of the present invention.

FIG. 21 shows characteristic graphs (schematic graphs) each showing a used dichroic mirror according to Embodiment 11 of the present invention.

FIG. 22(A) shows the fluorescence spectra of the fluorescent materials after being transmitted through or reflected on the dichroic mirror, and FIG. 22(B) is a table for describing computation results of the fluorescence intensity ratios of the fluorescent materials, according to Embodiment 11 of the present invention.

FIG. 23 is a graph for describing computation results of a relation between FRET efficiency and the fluorescence intensity ratios of respective fluorescent materials according to Embodiment 12 of the present invention.

[FIG. 24]FIG. 24(A) is a configuration view showing a fluorescence detecting apparatus, and FIG. 24(B) is a characteristic graph (schematic graph) showing a used dichroic mirror, according to Embodiment 12 of the present invention.

FIG. 25 shows a graph and a table for describing computation results of an expected relation between the FRET efficiency and the fluorescence intensity ratios of the respective fluorescent materials at the time of using the configuration and the dichroic mirror of FIG. 24 according to Embodiment 12 of the present invention.

[FIG. 26]FIG. 26(A) is a characteristic graph (schematic graph) showing a used dichroic mirror, FIG. 26(B) is a graph for describing computation results of an expected relation between FRET efficiency and the fluorescence intensity ratios of respective fluorescent materials, and FIG. 26(C) is a table for describing computation results of the fluorescence intensity ratios when the FRET efficiency is 50%, according to Embodiment 13 of the present invention.

[FIG. 27]FIG. 27 is a configuration view showing a fluorescence detecting apparatus according to Embodiment 14 of the present invention.

[FIG. 28]FIG. 28(A) is a characteristic graph (schematic graph) showing the fluorescence spectrum of a fluorescent material and a long-pass filter, and FIG. 28(B) is a graph for describing computation results of an expected relation between FRET efficiency and the fluorescence intensity ratios of respective fluorescent materials, according to Embodiment 15 of the present invention.

[FIGS. 29]FIG. 29(A) and 29(B) are characteristic graphs (schematic graphs) each showing another example long-pass filter and the fluorescence spectrum according to Embodiment 15 of the present invention.

FIG. 30 is a characteristic graph (schematic graph) showing another example dichroic mirror and the fluorescence spectrum according to Embodiment 15 of the present invention.

[FIG. 31]FIG. 31(A) is a characteristic graph showing the fluorescence spectra of other example fluorescent materials, and FIGS. 31(B) and 31(C) are characteristic graphs (schematic graphs) respectively showing the long-pass filter and the dichroic mirror, according to Embodiment 15 of the present invention.

DESCRIPTION OF EMBODIMENTS

Hereinafter, the present invention is described by way of embodiments, but the present invention is not limited to the embodiments.

Embodiment 1

Description is given of an apparatus and a method for capturing sample DNA fragments to be analyzed molecule by molecule at equal intervals on a substrate surface, elongating the captured fragments substantially for each base, detecting taken-in fluorescent labels molecule by molecule, and thus determining a nucleotide sequence thereof. Specifically, in one cycle, performed are: a step of causing a DNA polymerase reaction using four types of dNTP derivatives which can be each taken into a template DNA as a substrate of a DNA polymerase to stop a DNA chain elongation reaction by the presence of a protecting group, the dNTP derivatives each having a detectable label; then, a step of detecting the taken-in dNTP derivatives by fluorescence detection or the like; and a step of bringing the dNTP derivatives back into an elongatable state. Such a cycle of the steps is repeated to determine the nucleotide sequence of the sample DNA. Note that single-molecule fluorescence detection is performed in these steps, and hence it is desirable that the measurement be performed in a clean room environment via a HEPA filter or the like.

(Apparatus Configuration)

Figure 1:
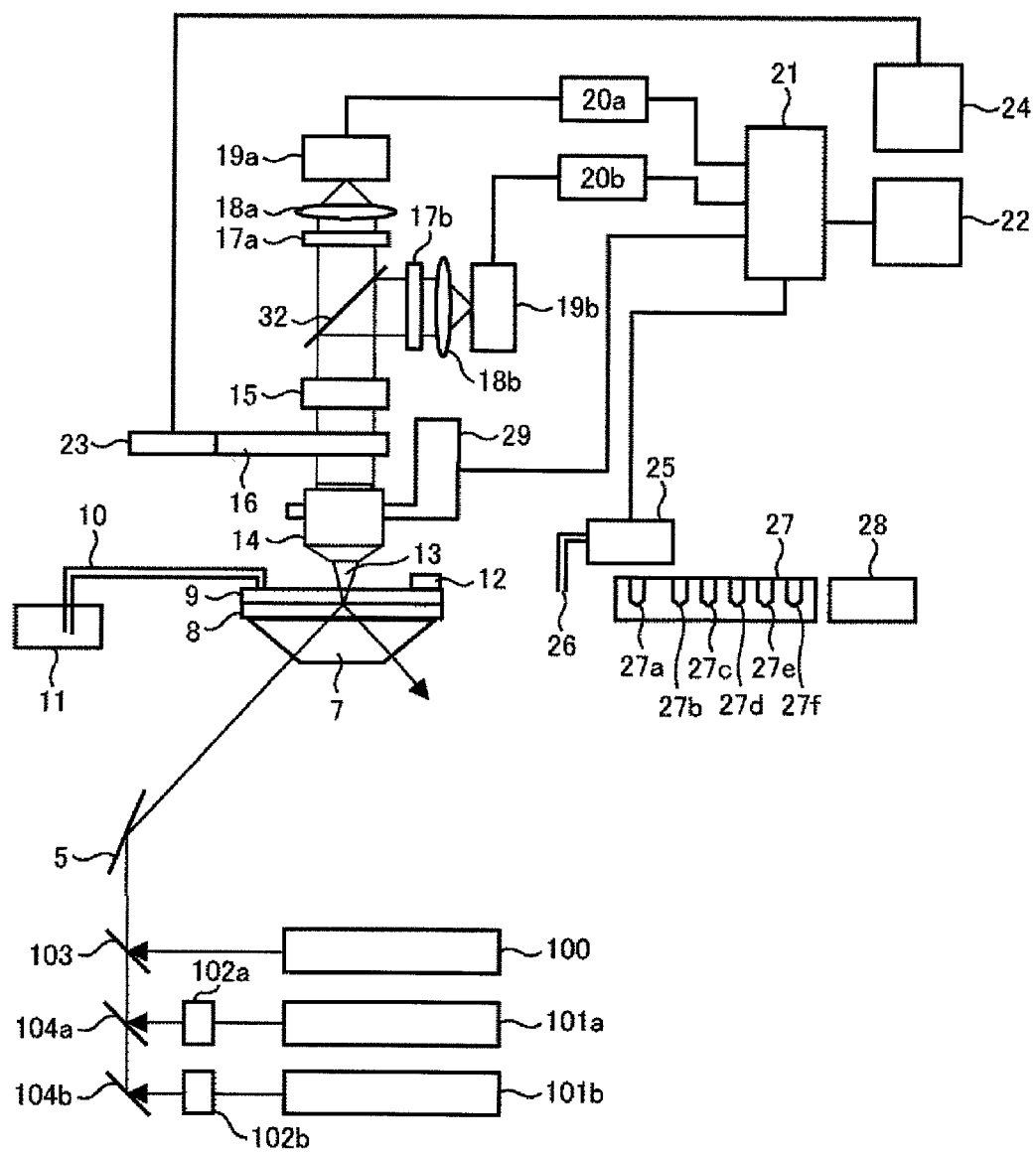
[FIG. 1]

FIG. 1 is a configuration view showing a DNA testing apparatus using a fluorescence analyzing method according to the present invention. The apparatus has an apparatus configuration similar to a microscope, and measures elongation states of DNA molecules captured on a substrate 8 by fluorescence detection.

The substrate 8 has a structure as shown in FIG. 2. At least part of the substrate 8 is made of a transparent material, and examples of the material of the substrate 8 include synthetic quartz. The substrate 8 includes a reaction region 8a, which is made of a transparent material, and a reagent and the like come into contact with the reaction region 8a. A plurality of regions 8ij for capturing DNA are formed in the reaction region 8a. The regions 8ij each have a diameter equal to or less than 100 nm. The regions 8ij are subjected to surface treatment for capturing DNA. For example, streptavidin is bound to the regions 8ij in the surface treatment, and biotinylated DNA fragments are reacted therewith, whereby DNAs can be captured. Alternatively, poly T oligonucleotides are captured therein, and one ends of the DNA fragments are changed to poly A, whereby DNAs can be captured by a hybridization reaction. At this time, only single-molecule DNA is allowed to enter each region 8ij by appropriately preparing the DNA fragment concentration. Note that the number of molecules which can be captured in each region can be made one by further reducing the size of each region 8ij. Hereinafter, the substrate in such a state is measured. With regard to the substrate as described above, there are cases where single-molecule DNA is captured in all the regions 8ij and where DNA is captured in only part of the regions 8ij. In the case where DNA is captured in only part of the regions 8ij, DNA is not captured in the other regions 8ij, and the other regions 8ij are vacant. Note that an interval dx between the regions 8ij is set to 2 micrometers, and an interval dy therebetween is set to 2 micrometers. The regions 8ij form a lattice structure (two-dimensional lattice structure) in this way, and the regions 8ij are disposed at lattice point positions of the lattice structure. Such a substrate including regions at equal intervals is produced according to, for example, a technique described in JP Patent Publication (Kokai) No. 2002-214142 A. Note that dx and dy are more than the size of each region 8ij, and dx and dy are preferably equal to or less than 0.2 to 10 micrometers and more preferably approximately 0.5 to 6 micrometers. Note that the lattice structure may be a square lattice structure, a rectangular lattice structure, a triangular lattice structure, and the like. The reaction region 8a of the substrate is set to a size of 1 mm×1 mm. The size of the reaction region 8a can be more than 1 mm×1 mm. The reaction region 8a may be configured by arranging a plurality of regions having a size of 0.5 mm×0.5 mm one-dimensionally or two-dimensionally at given intervals, or may have a rectangular shape, a circular shape, a triangular shape, a hexagonal shape, and the like. Note that a metal structure may be disposed in each region 8ij. The metal structure can be produced by semiconductor processing. The metal structure can be produced by techniques such as electron beam lithography, optical lithography, dry etching, and wet etching. The metal structure is made of gold, silver, aluminum, chromium, titanium, tungsten, platinum, or the like, and has a size equal to or less than the wavelength of excitation light. The shape of the metal structure may be a rectangular parallelepiped, a circular cone, a circular cylinder, a triangular prism, a structure having a protruding portion, or a structure in which two or more of these shapes are adjacently arranged, and metal fine particles can also be used for the metal structure. For example, gold film-like dots having a diameter of approximately 10 nm to 100 nm can be formed in a lattice pattern at the intervals dx and dy, for example, intervals of 1×1, 1×2, 1×3, 2×3, 2×4, 3×5, or 3×6 (micrometers×micrometers). If proteins, fluorescent substances, and linkers having a size of approximately 20 nm are captured at dots having a diameter of approximately 20 nm, stochastically, such a size enables one molecule to be captured at one dot, and single-molecules can be disposed in a lattice pattern. In addition, selective linkers are bound to the dots according to a known technique, and oligonucleotides, proteins, and the like are captured by the selective linkers, whereby target molecules can be captured for use at the dots.

Various fluorescent materials can be used for the fluorescent labels of dNTPs. For example, with the use of Bodipy-FL-510, R6G, ROX, and Bodipy-650, four types of dNTPs (3'-O-allyl-dGTP-PC-Bodipy-FL-510, 3'-O-allyl-dTTP-PC-R6G, 3'-O-allyl-dATP-PC-ROX, and 3'-O-allyl-dCTP-PC-Bodipy-650) are prepared, the four types of dNTPs being respectively labeled with these four different types of fluorescent materials and each having an allyl-modified 3' end. dNTPs modified with other fluorescent materials than these four types can also be used.

A laser beam from a laser apparatus 101a for fluorescence excitation (Ar laser, 488 nm: for excitation of Bodipy-FL-510 and R6G) is circularly polarized through a λ/4 wave plate 102a. A laser beam from a laser apparatus 101b for fluorescence excitation (He—Ne laser, 594.1 nm: for excitation of ROX and Bodipy-650) is circularly polarized through a λ/4 wave plate 102b. The two laser beams are superimposed on each other by a mirror 104b and a dichroic mirror 104a (which reflects a wavelength equal to or less than 520 nm), and the superimposed beam perpendicularly enters an incident surface of a quartz prism 7 for total-reflection illumination via a mirror 5 as shown in the Figure, and is radiated to a rear side of the substrate 8 for capturing DNA molecules. The quartz prism 7 and the substrate 8 are in contact with each other via matching oil (nonfluorescent glycerin or the like), and the laser beam is introduced into the substrate 8 without being reflected on an interface of the matching oil. A surface of the substrate 8 is covered by a reaction liquid (water), and the laser beam is totally reflected on an interface of the reaction liquid to become evanescent illumination. This enables fluorescence measurement with a high S/N ratio.

Note that a temperature controller is disposed in the vicinity of the substrate, but is not shown in the Figure. In addition, halogen illumination and LED illumination from below the prism are possible for normal observation, but are not shown in the Figure.

In addition, a laser apparatus 100 (YAG laser, 355 nm) is disposed separately from the laser apparatuses 101a and 101b, and a laser beam from the laser apparatus 100 is superimposed on the laser beams from the laser apparatuses 101a and 101b by a dichroic mirror 103 (which reflects a wavelength equal to or less than 400 nm) to be radiated with the axes of the beams being coincident with one another. The laser apparatus 100 is used in the step of bringing the dNTP derivatives back into an elongatable state, after the fluorescence detection of the taken-in dNTP derivatives.

A flow chamber 9 for flowing and reacting the reagent and the like is formed on the substrate 8. The chamber is provided with a reagent inlet 12, and a desired reagent solution is fed thereto using a dispensing unit 25 including a dispensing nozzle 26, a reagent storing unit 27, and a chip box 28. The reagent storing unit 27 includes a sample solution container 27a, dNTP derivative solution containers 27b, 27c, 27d, and 27e (27c, 27d, and 27e are spare containers), and a cleaning liquid container 27f. A dispensing chip in the chip box 28 is attached to the dispensing nozzle 26, and an appropriate reagent solution is sucked to be introduced for reaction into the reaction region of the substrate from the inlet of the chamber. Waste liquid is discharged to a waste liquid container 11 via a waste liquid tube 10. These are automatically performed by a control PC 21.

Figure 3:
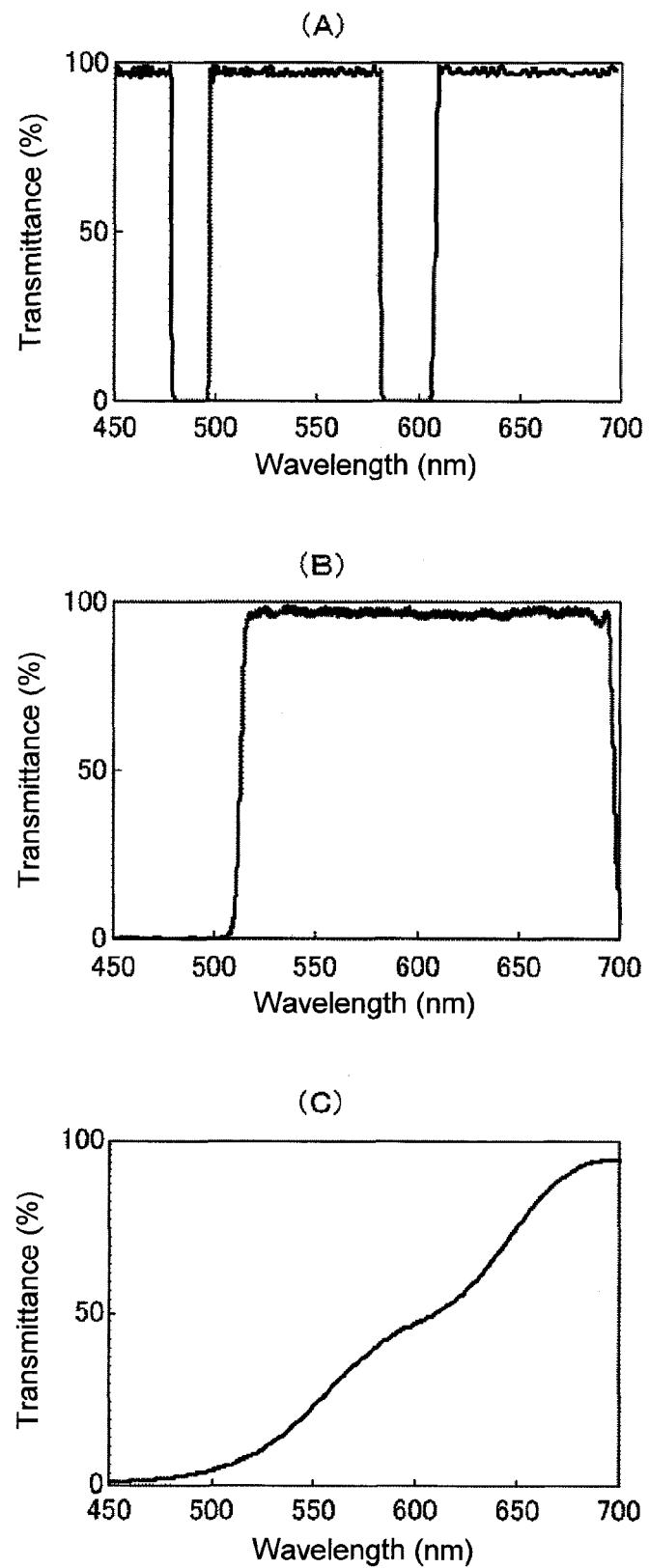
[FIG. 3]

The flow chamber is formed of a transparent material in an optical axis direction, for the fluorescent detection. Fluorescence 13 is collected by a light collecting lens (objective lens) 14 controlled by an automatic focusing apparatus 29. Fluorescence having a necessary wavelength is taken out of the fluorescence 13 by a filter unit 15. The fluorescence transmitted through the filter unit 15, which removes light having an unnecessary wavelength, is divided by a dichroic mirror 32 into light fluxes divided at ratios different for each wavelength. The divided light fluxes respectively pass through subsidiary filters 17a and 17b, and images of the divided light fluxes are respectively formed and detected by two-dimensional sensor cameras 19a and 19b (high-sensitivity cooled two-dimensional CCD cameras) via imaging lenses 18a and 18b. Exposure time setting of the cameras, capture timing control of the fluorescent images, and the like are performed by the control PC 21 via two-dimensional sensor camera controllers 20a and 20b. Note that two types of notch filters for laser beam removal (488 nm and 594.1 nm) and a bandpass interference filter which transmits a wavelength range to be detected (transmission range: 510 to 700 nm) are used in combination for the filter unit 15. FIG. 3(A) shows general characteristics of the notch filters for laser beam removal, FIG. 3(B) shows general characteristics of the bandpass interference filter (and the subsidiary filters 17a and 17b), and FIG. 3(C) shows general characteristics of the dichroic mirror 32.

Note that the apparatus includes a lens barrel 16 for transmitted light observation, a TV camera 23, and a monitor 24 for the purpose of adjustment and the like, and the state of the substrate 8 can be observed in real time using the halogen illumination.

As shown in FIG. 2(A), positioning markers 30 and 31 are provided on the substrate 8. The markers 30 and 31 are disposed parallel to the arrangement of the regions 8ij, and an interval therebetween is defined. Accordingly, the positions of the regions 8ij can be calculated by detecting the markers at the time of observation using transmission illumination.

CCD area sensors are used as the two-dimensional sensor cameras according to the present embodiment. The used CCD area sensors may have various pixel sizes and pixel counts. For example, cooled CCD cameras having a pixel size of 7.4×7.4 micrometers and a pixel count of 2,048×2,048 pixels are used as the two-dimensional sensor cameras. Note that image pick-up cameras such as C-MOS area sensors can be generally used as the two-dimensional sensor cameras, in addition to the CCD area sensors. There are CCD area sensors of back-side illumination type and front-side illumination type, which are different in structure, and both the types can be used. In addition, electron-multiplier CCD cameras having a function of multiplying signals inside of an element are advantageous to achieve higher sensitivity. In addition, cooled sensors are desirable, and dark noise of the sensors can be reduced by setting a temperature to approximately −20° C. or lower, so that the measurement accuracy can be increased.

The fluorescent images from the reaction region 8a may be detected at a time, or may be divided to be detected. In this case, an X-Y moving mechanism for moving the position of the substrate is disposed in a lower part of a stage, and movement to a radiation position, light radiation, and fluorescent image detection are controlled by the control PC. In the present embodiment, the X-Y moving mechanism is not shown.

(Reaction Step)

The step of a gradual elongation reaction is described below. The reaction step is performed by reference to Non Patent Literature 2 and Non Patent Literature 4. Buffers to which streptavidin is added are introduced into the chamber from the inlet 12, and streptavidin is bound to biotin captured on each metal structure, whereby biotin-avidin complexes are formed. Primers are hybridized to biotin-modified single-stranded template DNAs as targets, the resultant template DNA-primer complexes and buffers to which an excessive amount of biotin is added are introduced into the chamber, and the single-molecule template DNA-primer complexes are captured on the metal structure disposed at each lattice point, with the aid of the biotin-avidin binding. After the capture and reaction, surplus template DNA-primer complexes and biotin are washed away from the chamber by cleaning buffers. Next, four types of dNTPs (3'-O-allyl-dGTP-PC-Bodipy-FL-510, 3'-O-allyl-dTTP-PC-R6G, 3'-O-allyl-dATP-PC-ROX, and 3'-O-allyl-dCTP-PC-Bodipy-650) and Thermo Sequenase Reaction buffers to which Thermo Sequenase polymerases are added are introduced into the chamber from the inlet 12 to thereby cause the elongation reaction, the four types of dNTPs being respectively labeled with four different types of fluorescent materials and each having an allyl-modified 3' end. Because the dNTPs taken into the template DNA-primer complexes each have an allyl-modified 3' end, more than one base is not taken into the template DNA-primer complexes. After the elongation reaction, unreacted dNTPs and the polymerases are washed away by cleaning buffers, and the laser beams oscillated from the respective light sources of the Ar laser source 101a and the He—Ne laser source 101b are radiated to a chip at the same time. The fluorescent materials labeled to the dNTPs taken into the template DNA-primer complexes are excited by the laser radiation, and fluorescence generated therefrom is detected. The fluorescence wavelengths of the fluorescent materials labeled to the dNTPs taken into the template DNA-primer complexes are identified, whereby the base types of the dNTPs can be identified. Note that, because the evanescent illumination is adopted and the excitation light is illuminated to only a portion around the reaction region surface, the fluorescent materials existing in other region than the surface are not excited, and measurement with small background light can be achieved. Accordingly, although the cleaning is performed after the elongation reaction in the above-mentioned case, if the fluorescent label dNTP concentration is small, measurement can be performed without the cleaning in some cases.

Next, the laser beam oscillated from the YAG laser source 100 is irradiated to the chip, and the fluorescent materials labeled to the dNTPs taken into the complexes are removed by optical cutting. Subsequently, a solution containing palladium is introduced into the flow path, and the allyl group of the 3' end of each of the dNTPs taken into the complexes is changed to a hydroxyl group by a palladium-catalyzed reaction. The elongation reaction of the template DNA-primer complexes can be restarted by changing the allyl group of the 3' end to the hydroxyl group. After the catalyzed reaction, the chamber is cleaned by cleaning buffers. The sequence of each captured single-stranded template DNA is determined by repeating the above-mentioned processes.

In this system, light emissions from the plurality of regions 8ij of the reaction region 8a can be measured at the same time. Accordingly, in the case where different template DNAs are respectively captured in the regions 8ij, the base types of dNTPs taken into complexes of the plurality of different template DNAs and primers, that is, the sequences of the plurality of template DNAs can be determined at the same time.

(Fluorescence Detection and Fluorescent Material Identification)

Description is given of a method of detecting fluorescence of the fluorescent materials captured on the substrate, identifying fluorescent material types, that is, base types, and measuring the fluorescence intensities thereof.

In FIG. 1, an imaging magnification for the CCD cameras 19a and 19b is set to 14.8 times, and the plurality of regions 8ij (lattice points) for capturing DNA are subjected to fluorescence measurement. In this case, the fluorescence is detected by CCD pixels with the interval dx=2 micrometers being divided into four.

For example, in the case where wavelength dispersion is performed using a dispersive element, the smallest interval between the lattice points is 2 micrometers, and 500 to 700 nm which is a fluorescence emission wavelength range is dispersed in this range to obtain 50 nm per pixel. Because the fluorescence maximum wavelengths of the four types of fluorescent materials are about 510 nm, about 550 nm, about 610 nm, and about 650 nm, respectively, the pixel setting as described above causes fluorescence overlapping, and hence distinctive identification is difficult. Further, in an actually formed image, each region 8ij does not fall within one pixel, and the image thereof is formed over several pixels to make the overlapping larger, resulting in further difficult identification.

Figures 5, 6:
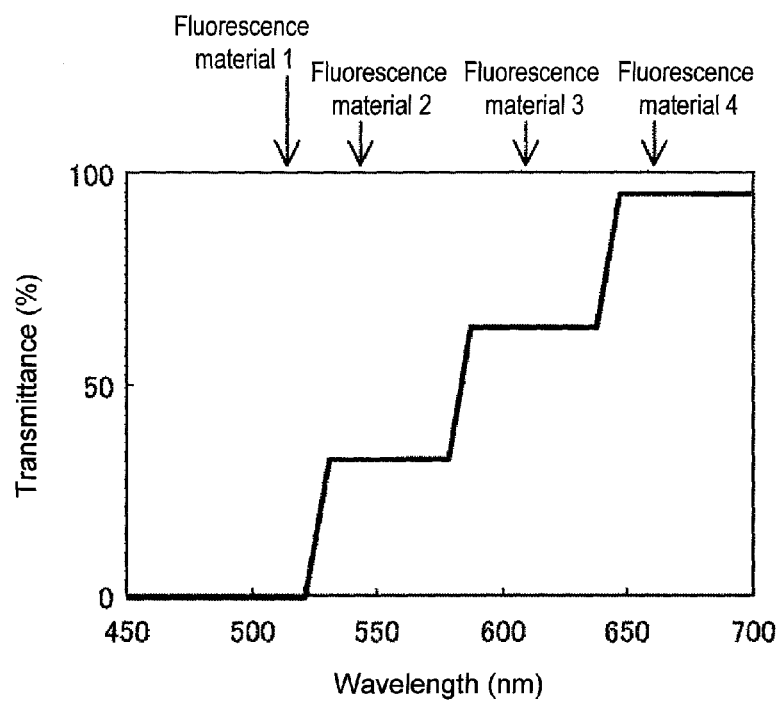
[FIG. 5]
[FIG. 6]

In the present embodiment, an image of a dot at which a fluorescent material molecule is captured, an image of light emitted from a position at which each fluorescent material molecule exists, and an image of each fluorescence emission point are formed without being dispersed, and hence the above-mentioned problem does not occur. FIG. 4 shows the outline of the fluorescence detection of the respective fluorescent materials. FIG. 4(A) shows the fluorescence emission spectra of the respective fluorescent materials, and FIG. 4(B) shows the fluorescence spectral components of the respective fluorescent materials which reach the two-dimensional CCD cameras 19a and 19b after passing through the filter unit 15, the dichroic mirror 32, and the subsidiary filters 17a and 17b according to the present embodiment. As shown in the figures, the fluorescent components of the respective fluorescent materials reach the two-dimensional CCD cameras 19a and 19b at different ratios. The two-dimensional CCD cameras do not obtain information on a wavelength direction and obtain only brightness information of a bright spot. Specifically, integral values of the spectra shown in FIG. 4(B) are calculated as the detected light intensities. As a result, the light intensities detected by the two-dimensional CCD cameras 19a and 19b are as shown in FIG. 5, and the ratio is different for each fluorescent material. The type of the fluorescent material can be identified on the basis of this ratio, and the fluorescence intensity of the fluorescent material, that is, the fluorescence intensity of the dot at which the fluorescent material is captured is calculated as the sum of the fluorescence intensities of corresponding bright spots of the two CCD cameras. In this way, the fluorescence intensity of one bright spot is divided using the dichroic mirror at ratios different for each wavelength, and the divided fluorescence intensities are detected by different pixels, whereby the four types of fluorescent materials can be identified for fluorescence detection. The control PC 21 extracts fluorescence bright spots of the regions 8ij from the images of the respective CCD cameras, computes the fluorescence intensity ratios thereof, and determines fluorescence from which fluorescent material each fluorescence bright spot corresponds to, to thereby identify the base types for sequence analysis.

Note that usable fluorescent materials are not limited to those described in the present embodiment, and the combination of fluorescent materials which exhibit different fluorescence characteristics using given excitation light can be similarly used. In general, the combination of fluorescent materials having different fluorescence maximum wavelengths may be used.

In addition, the number of two-dimensional CCD cameras does not necessarily need to be two, but may be one. In this case, when divided images are formed on the same two-dimensional CCD camera, the images are shifted to right and left such that the positions of the images are different from each other.

In the present embodiment, the number of the types of fluorescent materials is four, but can be three, five, six, or more.

In the present embodiment, the dichroic mirror 32 has a transmittance which is substantially linear from substantially 0% to substantially 100% in a specified wavelength range, but the transmittance of the used mirror may be substantially linear from substantially 10% to substantially 80%. Alternatively, the dichroic mirror 32 may be a dividing mirror having a transmittance and a reflectance which are different for each fluorescence maximum wavelength of the plurality of used fluorescent materials. For example, the dichroic mirror 32 can also be a mirror having characteristics which change in a stepwise manner for each fluorescence maximum wavelength (as schematically shown in FIG. 6). It is sufficient that the used mirror be capable of dividing light at ratios different for each fluorescence maximum wavelength or each wavelength exhibiting the maximum peak of the plurality of fluorescent materials as targets.

Note that, although background light exists in the fluorescence measurement, description is given above of signal components from which background light components are excluded.

In addition, the laser beam enters the incident surface of the quartz prism 7 perpendicularly, that is, at an incident angle of 0 degrees. With this configuration, even if the substrate and the prism are moved integrally, the laser radiation position does not come out of the observation field of view of the objective lens. Accordingly, the substrate and the prism can be integrated with each other, and various methods of coupling the prism and the substrate can be selected. Optical bonding as well as oil coupling is possible, and the apparatus configuration can be easily selected.

Note that, in the present embodiment, the number of fluorescent molecules bound to each reaction region of the substrate is one, and a plurality of different fluorescent molecules do not exist at the same position. Hence, according to the apparatus and the method of the present invention, fluorescent material types, that is, base types can be efficiently identified, and a high-density substrate can be dealt with.

According to the present embodiment, a plurality of objects to be measured are precisely disposed, and images of the objects to be measured are respectively formed at given pixels of a plurality of detectors including a plurality of pixels, and the fluorescence intensity ratio is measured for each detector. In this way, a larger number of types of fluorescent materials can be identified, and the fluorescence intensities thereof can be computed. In particular, three, four, or more types of fluorescent materials as the labeled objects can be identified and detected by one or two two-dimensional CCD cameras as the detectors. This can suppress the apparatus costs and enables molecule-by-molecule detection.

Note that, in the present embodiment, the wavelength range to be detected is 500 to 700 nm, but is not limited thereto. The wavelength range to be detected can be appropriately set to 400 to 600 nm, 400 to 700 nm, 600 to 850 nm, and the like in accordance with the wavelength range of a used fluorescent material. For example, in the case of using fluorescent materials of Alexa Fluor 635, Alexa Fluor 660, Alexa Fluor 700, and Alexa Fluor 750, the fluorescence emission wavelength range is 630 to 820 nm, and the specified wavelength range of the dichroic mirror is set to 650 to 780 nm. In general, the specified wavelength range thereof is 400 to 900 nm. Note that the characteristics of the dichroic mirror may be adjusted in a range between: around the fluorescence maximum wavelength of a fluorescent material type having the shortest fluorescence maximum wavelength; and around the fluorescence maximum wavelength of a fluorescent material type having the longest fluorescence maximum wavelength, among the used fluorescent material types. Adjustment strictly between the fluorescence maximum wavelengths is not necessary. It is sufficient to divide light at different ratios around the fluorescence maximum wavelengths of the respective fluorescent material types. In addition, if the intensity ratio of fluorescence emitted from a given fluorescent material is different from the fluorescence intensity ratios of other fluorescent materials, the plurality of fluorescent materials can be identified.

In the present embodiment, light for fluorescence measurement is radiated to a substrate on which biologically relevant molecules such as oligonucleotides are captured, fluorescence generated therefrom is collected, an image of the collected fluorescence is formed on a two-dimensional detector, and the two-dimensional detector performs fluorescence detection. The substrate is substantially transparent and includes a plurality of regions in which molecules are to be captured, and the regions are disposed at lattice point positions of a lattice structure. A necessary reagent, sample, and the like are reacted on the substrate. Fluorescent materials on the substrate are excited by a light source for light excitation and a radiation optical system which serve for total-reflection illumination. Fluorescence generated therefrom is collected by a fluorescence collecting system. Light fluxes of the collected fluorescence are divided by a light dividing section at ratios substantially different for each wavelength in a specified wavelength range. Images of the divided light fluxes are formed on a detector by the imaging optical system to be detected by the detector including a plurality of pixels. Further, a data processing section computes the fluorescence intensities of corresponding bright spots of the divided fluorescent images, and determines the fluorescent material types on the basis of the fluorescence intensity ratios. With this configuration, various fluorescent material types can be easily identified and detected.

In the present embodiment, the metal structures are formed on the substrate. In this case, the spatial position of each structure can be detected by detecting photoluminescence and light scattering of the structure, and the metal structure can be effectively utilized as a positional reference marker.

The size of regions (spots or regions of the lattice points) at the lattice point positions is set to a diameter equal to or less than 100 nm. It is preferable that the size thereof be at least equal to or less than ⅓ of an interval between the nearest lattice points. This enables easier optical resolution and easier identification. The regions for capturing the lattice point positions are set to approximately 10 nm to 30 nm, which is effective to capture single-molecules.

In addition, in the present embodiment, capture regions are disposed in a lattice pattern with given grid intervals on the used substrate. Such disposition in the lattice pattern facilitates identification of corresponding bright spots between a transmission image and a reflection image. The present embodiment can be applied to the case where the substrate on which the capture regions are disposed in the lattice pattern is not used. In the case where the capture positions are randomly dispersed, for example, the case where molecules are randomly dispersed to be captured, the corresponding bright spots may be determined by comparing two images with each other for pattern analysis or referring to reference markers. A similar effect can be obtained also in this way.

In addition, in the present embodiment, images are formed in the state where an interval between the capture regions disposed in the lattice pattern with given grid intervals is set to 4 pixels×4 pixels. Images are formed such that the size of the light emission points falls within 3 pixels×3 pixels, and the fluorescence intensities thereof can be computed. That is, fluorescence from each region is divided by the dichroic mirror into a reflected light image and a transmitted light image, the respective images are formed within 3×3 pixels, and the fluorescent material type existing in each region can be determined using 3×3×2=18 pixels or less. Also in the case where molecules are randomly dispersed to be captured, each molecule can be identified using 18 pixels or less. Accordingly, molecules captured at high density can be detected and identified with high efficiency. The fluorescence intensities of the light emission points may be computed using 4 pixels×4 pixels.

In the above description, the pixel count of the CCD is set to 4×4 pixels per light emission bright spot, but can be adjusted to 5×5 pixels, 5×4 pixels, 4×3 pixels, 3×3 pixels, and the like. Even in the case of detection using these pixel counts, molecules captured at high density can be detected and identified with high efficiency.

Embodiment 2

Figure 7:
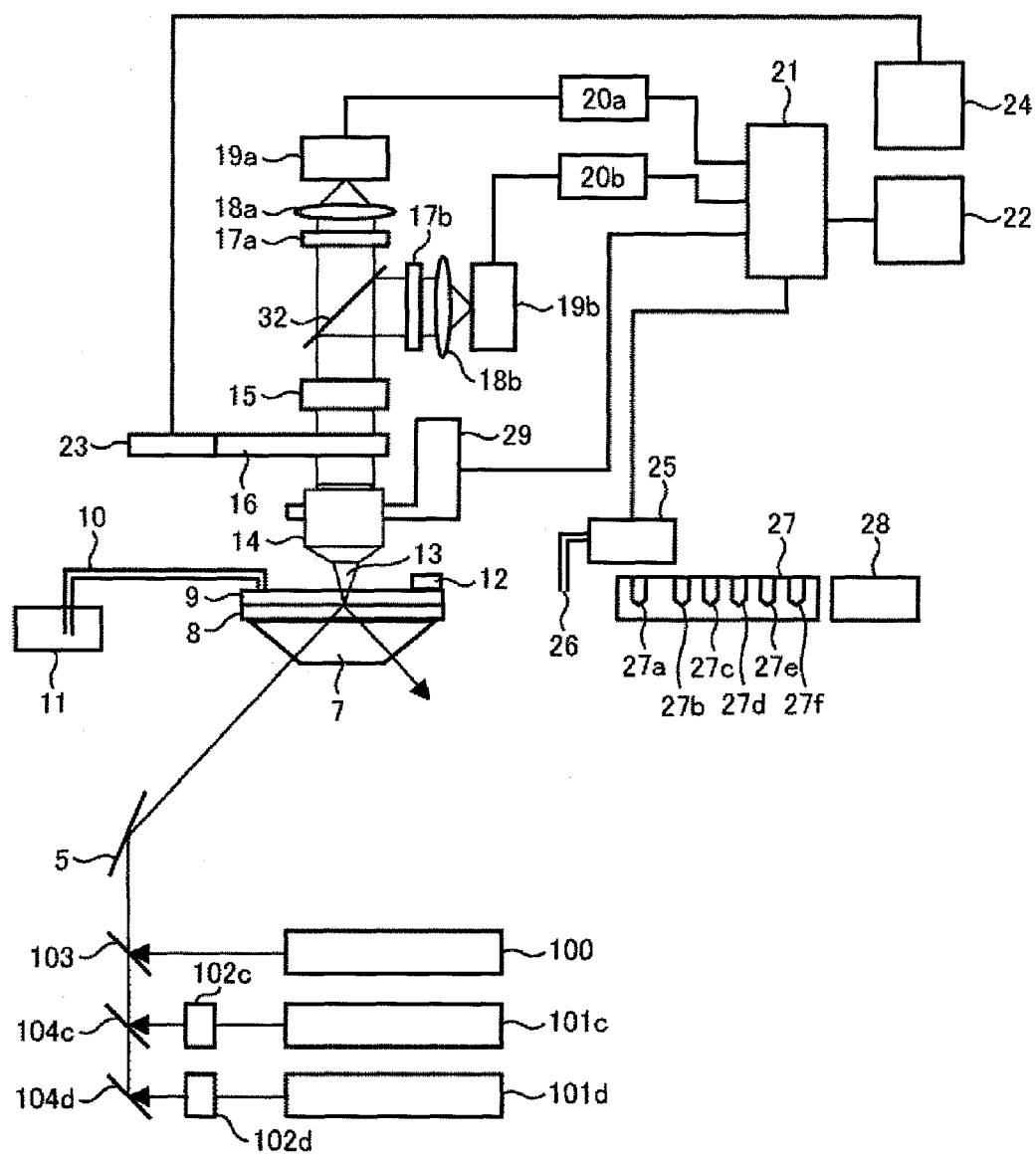
[FIG. 7]

FIG. 7 shows a configuration according to Embodiment 2 of the present invention. In the present embodiment, DNA sequencing is performed through a gradual elongation reaction using four types of fluorescent materials. An overall configuration and the like are the same as those of FIG. 1.

Alexa Fluor 488, Cy3, Cy5, and Cy5.5 are used for the fluorescent labels of dNTPs. Various fluorescent materials other than these can also be used therefor. In addition, four types of dNTPs labeled with one fluorescent material can also be used therefor. A laser beam from a laser apparatus 101c for fluorescence excitation (solid-state laser, 505 nm: for excitation of Alexa Fluor 488 and Cy3) is circularly polarized through a λ/4 wave plate 102c. A laser beam from a laser apparatus 101d for fluorescence excitation (semiconductor laser, 635 nm: for excitation of Cy5 and Cy5.5) is circularly polarized through a λ/4 wave plate 102d. The two laser beams are superimposed on each other by a mirror 104d and a dichroic mirror 104c (which reflects a wavelength equal to or less than 520 nm), and the superimposed beam perpendicularly enters the incident surface of the quartz prism 7 for total-reflection illumination via the mirror 5 as shown in the Figure, and is radiated to the rear side of the substrate 8 for capturing DNA molecules. The quartz prism 7 and the substrate 8 are in contact with each other via the matching oil (nonfluorescent glycerin or the like), and the laser beam is introduced into the substrate 8 without being reflected on the interface of the matching oil. The surface of the substrate 8 is covered by the reaction liquid (water), and the laser beam is totally reflected on the interface of the reaction liquid to become evanescent illumination. This enables fluorescence measurement with a high S/N ratio.

In the present embodiment, the same components as those of FIG. 1 are used, except that two types of notch filters for laser beam removal (505 nm and 635 to 642 nm) and a bandpass interference filter which transmits a wavelength range to be detected (transmission range: 510 to 700 nm) are used for the filter unit 15.

A method of determining a sequence is described according to actual measurement procedures. M13-DNA fragments are used as model samples. An end of each M13-DNA fragment is biotinylated according to a known method. A biotinylated DNA solution is kept in the sample solution container 27a of FIG. 7, and solutions (containing polymerases) of caged dATP labeled with Alexa Fluor 488, caged dCTP labeled with Cy3, caged dGTP labeled with Cy5, and caged dTTP labeled with Cy5.5 are mixed and kept in the container 27b. Note that the labeled caged dNTPs are caged compounds in which a 2-nitrobenzyl group is bound to a nucleotide, and the labeled caged dNTPs are each taken in as a complementary strand by the polymerases, but are suppressed from being continuously taken in due to a complementary strand synthesis reaction. Accordingly, the reaction is stopped after elongation of one base. Subsequently, if ultraviolet light equal to or less than 360 nm is radiated, a caged substance (2-nitrobenzyl group) is liberated, and an intrinsic activity of the nucleotide occurs, so that the next dNTP synthesis can be caused.

Biotinylated DNAs as templates are introduced into the flow chamber by the dispensing unit 25 to be reacted with the substrate. After cleaning, oligo primers are introduced to be hybridized to the biotinylated DNAs. This causes a complementary strand elongation reaction. First, after cleaning, the labeled caged dNTP solution is introduced. A base to be taken in is determined by a base of the next template at a primer binding position. The laser beams from the laser apparatuses 101c (505 nm) and 101d (635 nm) are radiated, and fluorescence measurement is performed by the two-dimensional sensor cameras. Similarly to Embodiment 1, the taken-in base can be identified by the presence or absence of fluorescence and the difference in fluorescence wavelength. Subsequently, the laser beam from the laser apparatus 100 (355 nm) is radiated to regain the activity of dATP. These procedures are performed in a plurality of cycles, whereby the nucleotide sequence can be determined.

In the present embodiment, the fluorescently-labeled caged dNTPs are used for the reagent which is capable of bringing the four types of dNTP derivatives back into an elongatable state according to measures of some kind, the four types of dNTP derivatives being each taken into a template DNA as a substrate of a DNA polymerase to stop a DNA chain elongation reaction by the presence of a protecting group and each having a detectable label. Alternatively, the present embodiment can be similarly implemented using a dNTP derivative in which a fluorescent material and a nucleotide are bound to each other by disulfide-bonding. In this case, the elongation is stopped by the presence of the fluorescent material, and the disulfide-bonding is chemically dissociated by a reagent of Tris[2-carboxyethyl]phosphine, whereby the dNTP derivative can be brought back into an elongatable state.

The present embodiment produces a substantially similar effect to that of Embodiment 1.

Embodiment 3

Another example combination of fluorescent materials is described.

A similar operation to that of Embodiment 1 can be easily performed using, as the fluorescent materials, five types of Alexa Fluor 488, Alexa Fluor 532, Alexa Fluor 568, Alexa Fluor 594, and Alexa Fluor 647, and these five types of fluorescent materials can be easily identified on the basis of the fluorescence intensity ratios, using the same dichroic mirror as that of FIG. 3(C).

Embodiment 4

An apparatus including three sensors is described. An application example thereof is described.

Figure 8:
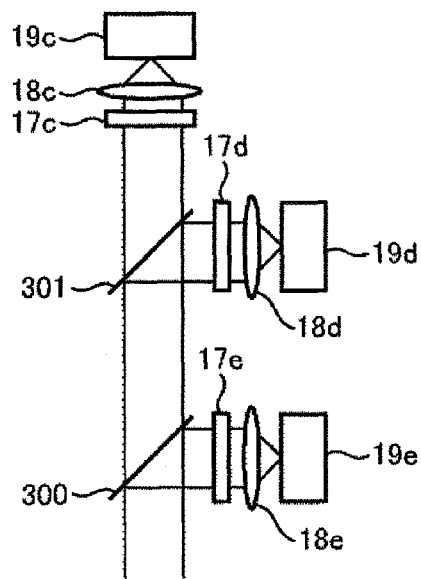
[FIG. 8]

FIG. 8 shows an apparatus configuration of a section which separates collected fluorescence. Two dichroic mirrors 300 and 301 are disposed as shown in the Figure. The fluorescence is divided by the dichroic mirrors 300 and 301 at predetermined ratios, images of the divided fluorescence fluxes are formed by imaging lenses 18c, 18d, and 18e, and the formed images are respectively detected by two-dimensional sensor cameras 19c, 19d, and 19e (high-sensitivity cooled two-dimensional CCD cameras). The control method is the same as that of Embodiment 1.

Figure 9:
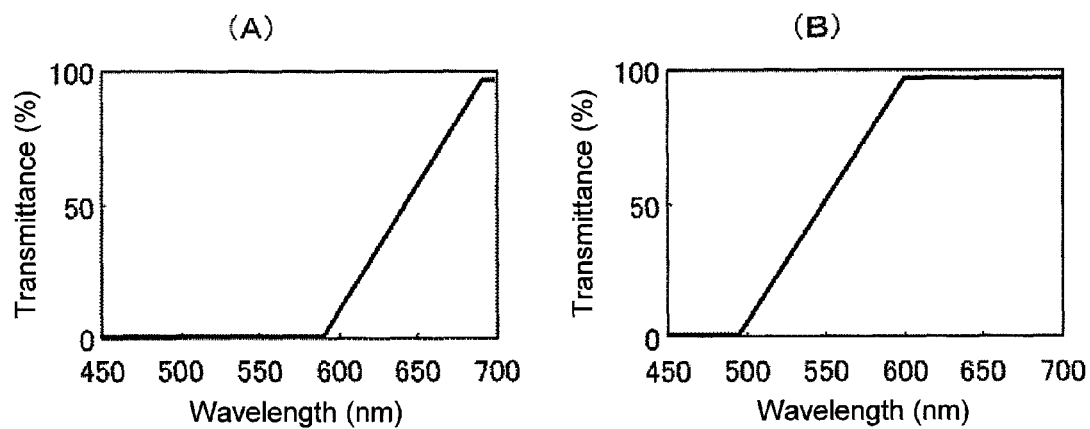
[FIG. 9]

FIG. 9 shows transmission (reflection) characteristic graphs showing the dichroic mirrors 300 and 301 in this case. As shown in the figures, the combination of ratios different for each wavelength is applied to the three types of cameras, whereby fluorescent materials having the fluorescence maximum wavelength in a range of 500 nm to 700 nm can be identified and detected. In the present embodiment, the combination of fluorescent materials according to Embodiment 3 can be identified.

Note that, in the present embodiment, the fluorescence wavelength range is assumed to be 500 to 700 nm, but is not limited thereto. The fluorescence wavelength range can be appropriately set to a range of 400 to 600 nm, a range of 400 to 700 nm, a range of 600 to 850 nm, and the like, similarly to Embodiments 1 and 2. For example, a fluorescent material having a fluorescence wavelength of 400 to 500 nm, such as Alexa Fluor 350, is used, and the specified wavelength range of the dichroic mirror is set to 400 to 700 nm, whereby fluorescent materials in a wider range can be similarly used. In the case of using fluorescent materials of Alexa Fluor 635, Alexa Fluor 660, Alexa Fluor 700, and Alexa Fluor 750, the fluorescence wavelength range is 630 to 820 nm, and the specified wavelength range of the dichroic mirror is set to 650 to 780 nm. In general, the specified wavelength range is 400 to 900 nm.

Embodiment 5

Figure 10:
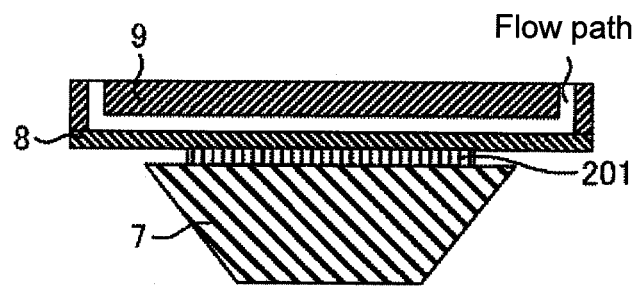
[FIG. 10]

FIG. 10 shows another structure of the joint part between the substrate and the prism for evanescent illumination. Similarly to FIG. 1, the substrate 8 is coupled to the quartz prism 7. The substrate 8 is joined thereto via a transparent elastic body as a coupling member, for example, a PDMS resin 201 (having a refractive index of 1.42, an internal transmittance of 0.966, and a thickness of 2 mm). Because the PDMS resin has a refractive index close to that of glass and is transparent, optical bonding is achieved by sandwiching and pushing the PDMS resin between the substrate and the prism. During the measurement, the measurement field of view on the substrate can be moved together with the prism by an X-Y stage.

Figure 11:
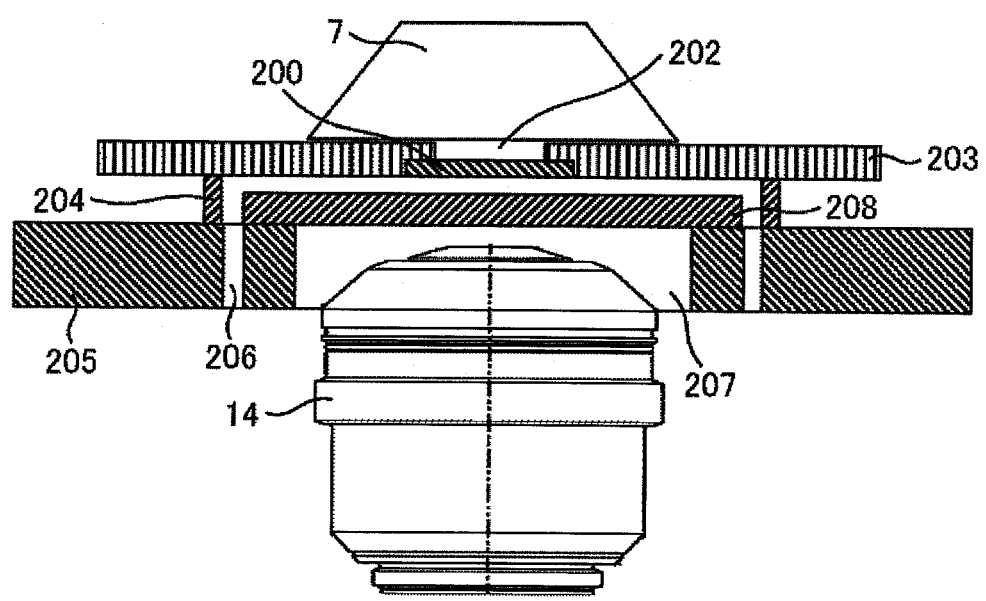
[FIG. 11]
Figure 12:
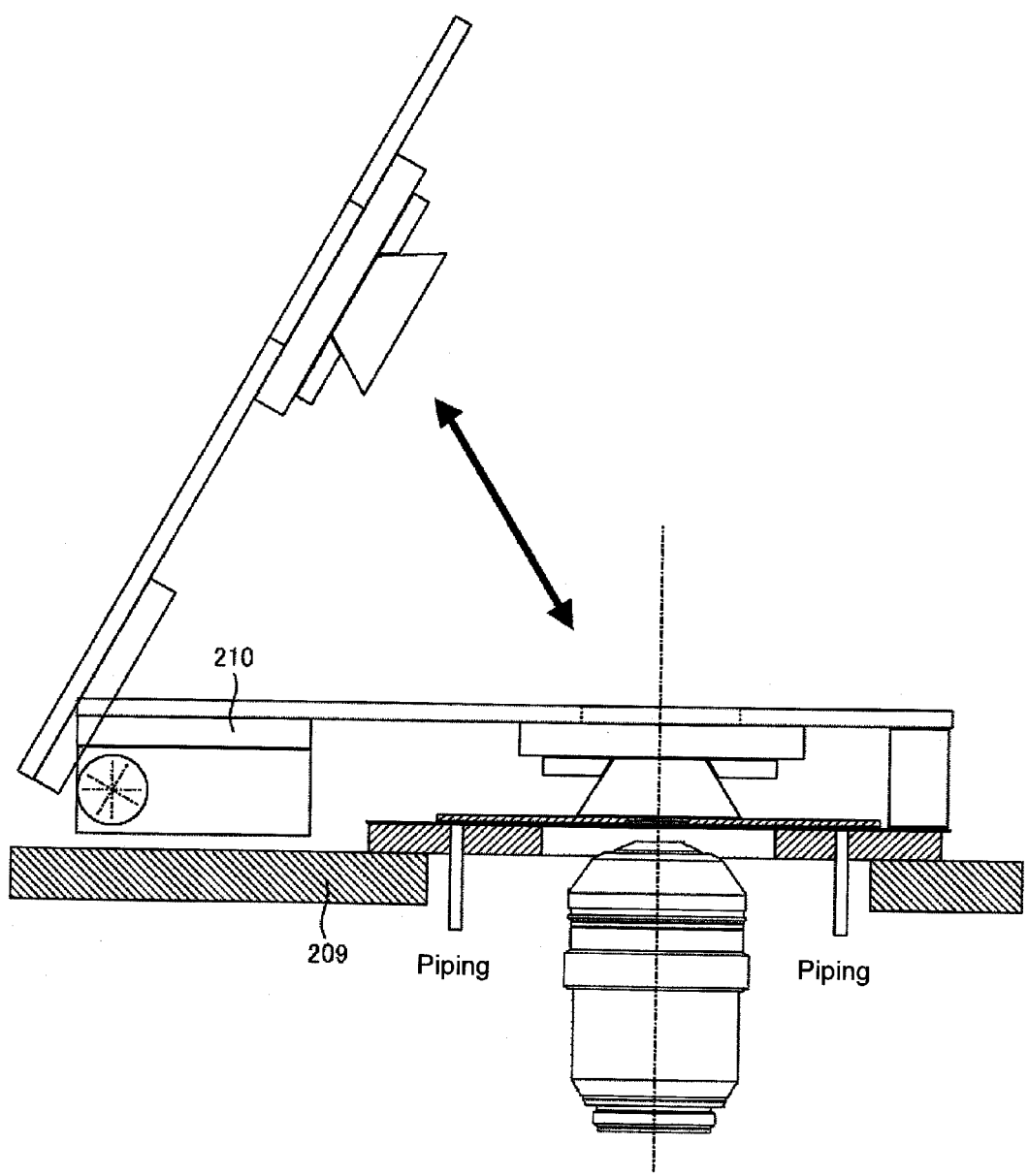
[FIG. 12]

FIG. 11 and FIG. 12 each show another structure of the joint part between the substrate and the prism for evanescent illumination.

A measurement substrate 200 is embedded and held in a dedicated holder 203. A flow chamber 204 is formed below the measurement substrate 200 (on a reaction surface side, a lattice structure formation side). The flow chamber 204 is formed of PDMS and is bonded to the holder 203 and the measurement substrate 200, and a reagent, a cleaning liquid, and the like can flow into a reaction region of the measurement substrate 200. This structure is brought into contact with a substrate holding tool 205 held by an X-Y stage 209 (shown in FIG. 12). The position of a flow path 208 of the flow chamber 204 is adjusted to coincide with the position of a through-hole 206. The through-hole 206 is connected to an external flow system. In addition, the substrate holding tool 205 includes a large opening 207 at the center thereof, and the opening 207 allows the light collecting lens 14 to come close to the measurement substrate 200, so that fluorescence can be collected with high efficiency.

Matching oil is kept in a hollow 202 inside of the holder 203 on a rear surface (the upper side in the figures) of the measurement substrate 200, and the prism 7 is disposed thereon. The matching may be achieved by filling the hollow 202 with a PDMS resin instead of the matching oil.

The prism 7 is held by a prism holder 210, and can be attached to and detached from the substrate. At the time of evanescent illumination, the prism 7 is bonded to the substrate.

Note that the prism may be made of acrylic or the like, and an integral structure of such an acrylic prism and the substrate can also be used.

The present embodiment can be similarly implemented by a configuration obtained by turning the structure shown in the figures upside down.

Embodiment 6

Figure 13:
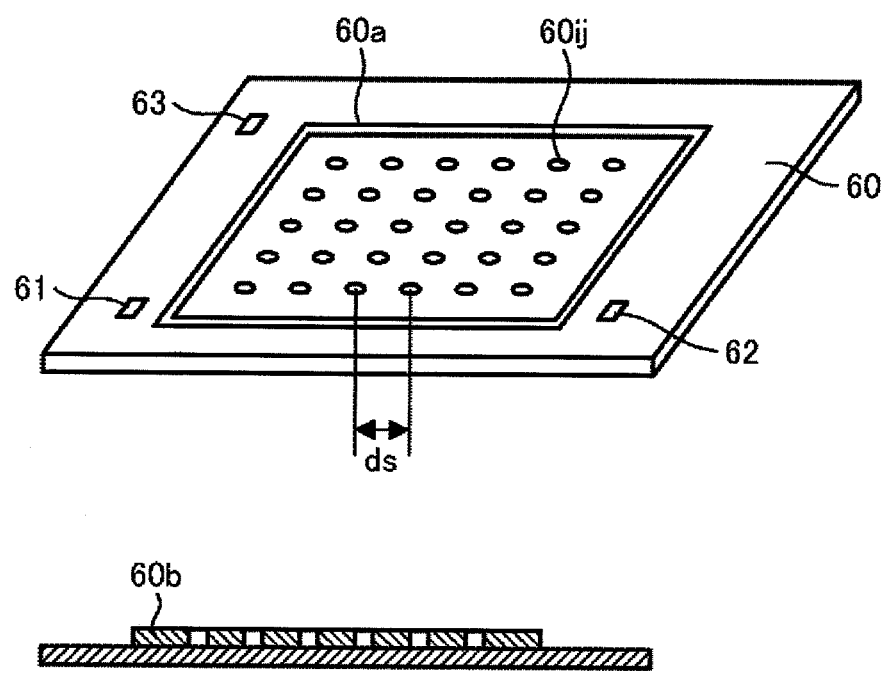
[FIG. 13]

Another embodiment of the reaction substrate is described. A structure of a substrate 60 according to the present embodiment is shown in FIG. 13. The substrate 60 includes a reaction region 60a, a plurality of regions 60ij for capturing DNA, proteins, and the like are formed at a pitch ds in the reaction region 60a, and the plurality of regions 60ij are each surrounded by an optically opaque mask 60b. Examples of the mask material include metal such as aluminum and chromium and silicon carbide, and the mask material is formed into a thin film by vapor deposition or the like. The regions 60ij each have a diameter equal to or less than 100 nm. Such openings are formed in the mask 60b by vapor deposition using a projection method (the vapor deposition is performed with an appropriate mask being disposed between a vapor deposition source and a substrate) or direct writing using electron beam lithography or photolithography. Dry etching or wet etching may also be used therefor.

In the case of the metal thin-film substrate including fine openings, biological molecules are captured in the openings. In this case, the spatial position of each metal structure can be detected by detecting Raman scattering light of a sample solution around the biological molecules and photoluminescence and light scattering of the metal structure near the biological molecules, and the metal structure can be utilized as a positional reference marker.

A metal structure may be provided in each opening. Similarly to Embodiment 1, positional markers 61, 62, and 63 can be disposed, whereby a similar effect to that of Embodiment 1 can be expected.

The present embodiment can produce a similar effect to that of Embodiment 1. In addition, because a portion other than the reaction regions 60ij is covered by the mask, unnecessary stray light and fluorescence can be reduced, and the measurement can be performed with higher sensitivity.

Embodiment 7

Description is given of the case where six types of fluorescent materials are used as labels. The mechanism concerning reactions is similar to those of the above-mentioned embodiments, and hence an optical measuring system is mainly described.

Figure 14:
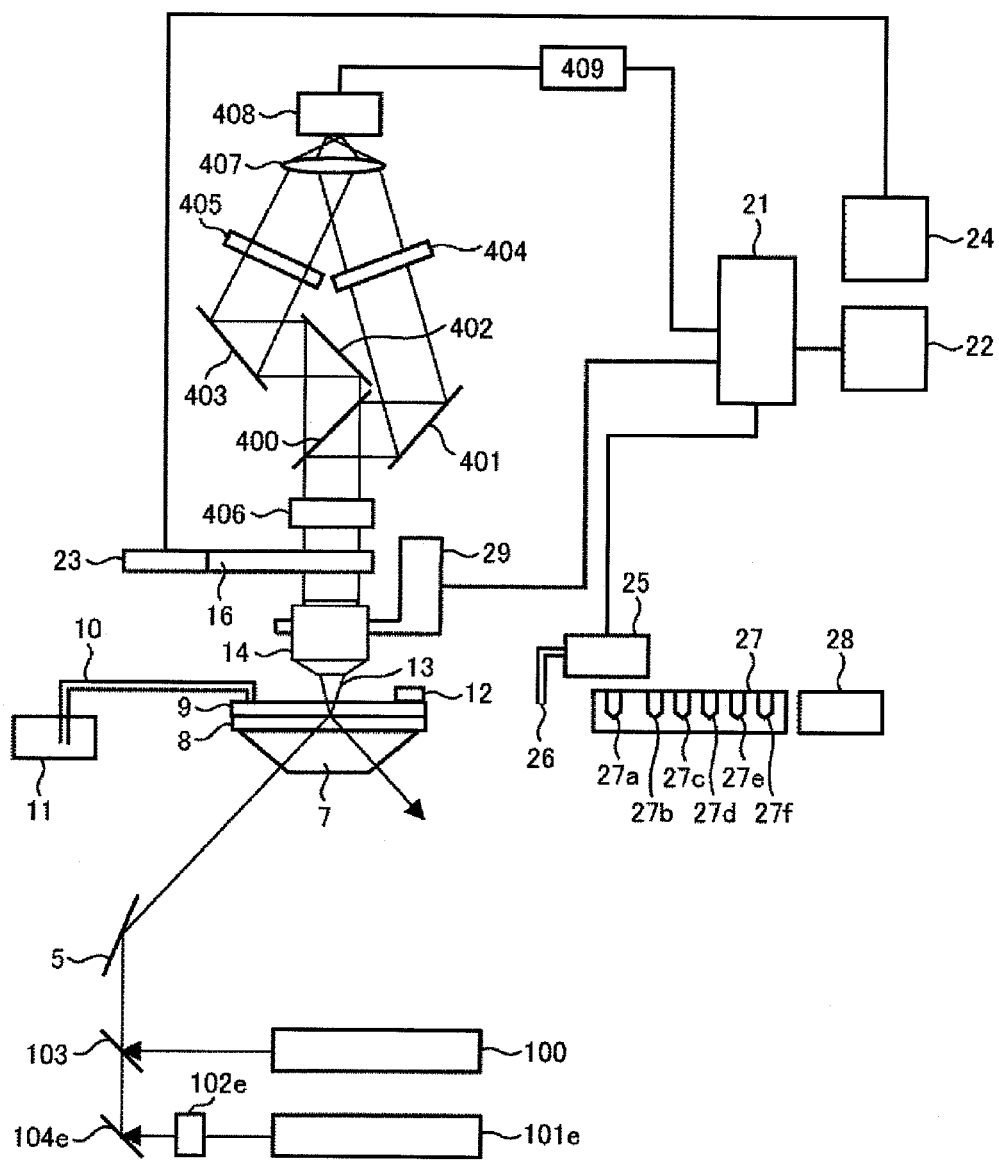
[FIG. 14]

FIG. 14 is a configuration view showing an apparatus using the fluorescence analyzing method according to the present invention. The reaction section, the objective lens of the laser radiation mechanism, and the like are the same as those of Embodiment 1 shown in FIG. 1.

Similarly with regard to the dot configuration of the substrate, in the present embodiment, the interval dx between the regions 8*ij* is set to 2 micrometers, the interval dy therebetween is set to 2 micrometers, and the dot diameter of the regions 8*ij* is set to 20 nm. A sample to be measured is captured in a single-molecule state at each dot.

Six types of Qdot 525, Qdot 565, Qdot 605, Qdot 625, Qdot 655, and Qdot 705 are used as fluorescent materials for labeling. Antibodies respectively labeled with these fluorescent materials are prepared to be reacted, and the respective fluorescent materials are captured at the dots disposed in a lattice pattern.

A laser beam from a laser apparatus 101*e* for fluorescence excitation (semiconductor laser, 405 nm) is circularly polarized through a λ/4 wave plate 102*e*. The laser beam perpendicularly enters the incident surface of the quartz prism 7 for total-reflection illumination via a mirror 104*e* and the mirror 5 as shown in the Figure, and is radiated to the rear side of the substrate 8 on which the fluorescent materials are captured.

The quartz prism 7 and the substrate 8 are optically bonded to each other via an adhesive, and the laser beam is introduced into the substrate 8 without being reflected on an interface of the adhesive. The surface of the substrate 8 is covered by the reaction liquid (water), and the laser beam is totally reflected on the interface of the reaction liquid to become evanescent-field illumination. This enables measurement of the fluorescent materials captured on the surface of the substrate 8 with a high S/N ratio. Note that, if the substrate 8 having an end face formed into a prismatic shape is used, the need to use the quartz prism 7 is eliminated, leading to a more simplified configuration.

The flow chamber 9 for flowing or keeping the reaction liquid containing a reagent and the like is formed on the substrate 8. The flow chamber is formed of a transparent material in the optical axis direction. The fluorescence 13 emitted from the substrate surface is collected by the light collecting lens (objective lens) 14 through the chamber 9, and is introduced into a dividing/imaging optical system through a filter unit 406. A short-wavelength cut filter (which cuts light in a wavelength range equal to or less than 450 nm at a transmittance of 0.000001 or less, and has a transmittance of 90% or more in a wavelength range equal to or more than 480 nm) and a bandpass interference filter (transmission range: 500 to 700 nm, transmittance: 90% or more) are used in combination for the filter unit 406. The short-wavelength cut filter serves to block the laser beam from the laser apparatus 101*e*, and the bandpass interference filter serves to set and transmit a fluorescence wavelength range to be detected. A notch filter (blocking wavelength: 450 nm±4 nm, transmittance: 0.000001 or less) which cuts light of 405 nm may be used therefor instead of the short-wavelength cut filter.

In the dividing/imaging optical system, first, the light is divided into transmitted light and reflected light at ratios different for each wavelength by a dichroic mirror 400 for division. Of the divided light fluxes, the reflected light is reflected on a mirror 401 to be guided to an imaging lens 407 at a specified angle, whereas the transmitted light is bent by mirrors 402 and 403 to be guided to the same imaging lens 407 at another specified angle. The two light fluxes enter the imaging lens at the different angles, to thereby form images on a two-dimensional sensor camera 408 (high-sensitivity cooled two-dimensional CCD camera) with the images being shifted from each other. Subsidiary filters 404 and 405 serve to remove stray light, and bandpass interference filters (transmission range: 500 to 700 nm, transmittance: 90% or more) are used for the subsidiary filters 404 and 405. The subsidiary filters do not necessarily need to be used. The images formed on the two-dimensional sensor camera 408 are collected and analyzed by the control PC 21 via a two-dimensional sensor camera controller 409. Note that the lengths of optical paths of the divided transmitted light and the divided reflected light are set to be as equal to each other as possible, but do not necessarily need to be equal to each other. In the Figure, imaging magnifications of the two light fluxes are the same as each other, but may be different from each other. The analysis is possible as long as the divided transmitted light image and the divided reflected light image deriving from the same bright spot can be identified.

FIG. 15 shows characteristic graphs showing the fluorescent materials and the dichroic mirror according to the present embodiment. FIG. 15 shows the fluorescence spectra (normalized) of the six types of Qdot 525, Qdot 565, Qdot 605, Qdot 625, Qdot 655, and Qdot 705 and a transmission characteristic of the dichroic mirror.

FIG. 16 shows schematic views for describing image acquisition according to the present embodiment. Wavelength components of the light reflected on the dichroic mirror 400 are shown in a graph of "FLUORESCENCE SPECTRUM OF DIVIDED REFLECTED LIGHT FLUX" in the right part of FIG. 16(A), and wavelength components of the light transmitted through the dichroic mirror 400 are shown in a graph of "FLUORESCENCE SPECTRUM OF DIVIDED TRANSMITTED LIGHT FLUX" in the left part of FIG. 16(A). Similarly to Embodiment 1, the light is divided into the transmitted light flux and the reflected light flux at ratios different for each wavelength. In the present embodiment, the reflection and transmission characteristics of the dichroic mirror change substantially linearly with respect to the wavelength. Note that, because the transmission range of the filter unit 406 is 500 to 700 nm, the wavelength range shown in each graph is also 500 to 700 nm.

Because the reflected light and the transmitted light enter the imaging lens 407 at the different angles, the fluorescent images of the respective lights can be formed at different positions in the same two-dimensional sensor camera 408, and the fluorescent images can be detected in a dual-view state. An imaging state of the fluorescence generated from the respective regions at the lattice point positions on the substrate is schematically shown in an upper view of FIG. 16(A). FIG. 16(B) shows part of a divided transmitted light intensity image (left view) and part of a divided reflected light intensity image (right view) of the fluorescent images of the bright spots deriving from the capture regions of the respective fluorescent materials arranged at the lattice points. The bright spot images indicated by circles in the Figure correspond to the divided transmitted light image and the divided reflected light image of the same bright spot. Depending on capture states of the fluorescent materials, fluorescence is not observed from all the capture regions arranged at the lattice points, and there are some portions without a bright spot.

FIG. 17 shows example computation results of fluorescence intensity ratios of the respective bright spots in FIG. 16(B). FIG. 17 shows the ratio of the divided transmitted light intensity and the ratio of the divided reflected light intensity to the sum of the divided transmitted light intensity and the divided reflected light intensity, for representative bright spots of the respective types of fluorescent materials. The respective spots correspond to the fluorescent material types indicated in the Figure. The respective fluorescent materials are detected at different ratios, and thus can be detected distinctively from one another. According to the present embodiment, the six types of fluorescent materials can be identified by one two-dimensional sensor camera, and hence a large number of types of fluorescent materials can be easily identified and detected at the same time.

The present embodiment can be applied to a protein chip with an antigen or antibody as a measurement target, a DNA chip, an antigen testing apparatus, and the like. Because six types of labels can be used at the same time, six types of labeled antibodies and the like are prepared to be reacted at the same time, reaction results thereof are measured at the same time, the labeled antibodies are identified on the basis of the ratios thereof, and the fluorescence intensities of the respective labeled antibodies can be computed. Not only single-molecule measurement but also quantitative determination is possible. Note that the positions of antibodies or antigens to be captured on the substrate do not necessarily need to be in a lattice pattern, and hence various chips can be dealt with. It goes without saying that the number of the types of labels is not limited to six, but may be three, four, or more.

In addition, the present embodiment can also be applied to cell staining, a cell chip, and the like. For example, antibodies which are specifically bound to cell surface antigens are prepared to be respectively labeled with fluorescent materials. Six types of the labeled antibodies are reacted at the same time, and are subjected to fluorescence measurement at the same time, whereby the distribution, concentration, and the like of the six types of antibodies can be measured. Not only such surface antigens but also cytoplasm markers, membrane markers, DNA, RNA, and the like can be detected at the same time.

Embodiment 8

Description is given of an example in which a divided transmitted light intensity image and a divided reflected light intensity image of the fluorescent images of the bright spots are formed and analyzed in a manner different from that of FIG. 16(B), the bright spots deriving from the capture regions of the respective fluorescent materials arranged at the lattice points.

FIG. 18 shows schematic views for describing an image dividing/detecting method. Description is given of the case where the interval dx between the lattice-like capture regions on the substrate is set to 3 micrometers, the interval dy therebetween is set to 2 micrometers, the dot diameter of the capture regions is set to 20 nm, and a sample to be measured is captured in a single-molecule state at each dot. The used two-dimensional sensor camera (high-sensitivity cooled two-dimensional CCD camera) has: a pixel size of 6.45×6.45 micrometers; a horizontal (x-directional) pixel count of 1,392 pixels; and a vertical (y-directional) pixel count of 1,040 pixels. The total magnification of the light collecting optical system and the imaging optical system is set to 12.9 times, whereby the intervals between the capture regions are 6 pixels in the dx direction and 4 pixels in the dy direction.

If the incident angles of the divided transmitted light flux and the divided reflected light flux to the imaging lens are made shallower in FIG. 14 or FIG. 16(A), images of the corresponding bright spots can be brought closer to each other as shown in FIG. 18(A). That is, the divided transmitted light image and the divided reflected light image are formed so as to be slightly shifted from each other in the dx direction. This makes the correspondence between the bright spots clearer, leading to facilitation of the analysis. Because the transmitted light image and the reflected light image overlap with each other, it is normally difficult to measure the fluorescence bright spots. In the present embodiment, however, the fluorescence bright spots are arranged in a lattice pattern, and hence the measurement thereof is possible by such adjustment that bright spot images to be superimposed are formed in the middle of the respective intervals between the other bright spot images. The present embodiment adopts a rectangular lattice pattern in which the interval dx between the capture regions on the substrate is longer than the interval dy therebetween. The transmission image and the reflection image are shifted from each other in the dx direction by about half the lattice pitch, whereby the bright spots are suppressed from overlapping with one another and thus can be efficiently detected and identified.

In the present embodiment, with regard to each of the divided transmitted light image and the divided reflected light image, the size of the fluorescent images of the respective bright spots is equal to or less than 3 (dx direction)×3 (dy direction) pixels in consideration of influences of image blurring and the like. Accordingly, the respective bright spots are detected using 3×3×2=18 pixels or less, and the fluorescent material types can be determined, so that a high-density substrate can be efficiently detected and analyzed. Alternatively, the fluorescence intensities of the respective bright spots may be computed using 4×3×2=24 pixels or less.

In addition, the dy-directional pixel count of the CCD is set to 4 pixels per light emission bright spot in the above description, but can be adjusted to 5 pixels, 3 pixels, and the like. Similarly, the dx-directional pixel count is not limited to 6 pixels. A high-density substrate can be also efficiently detected and analyzed using these other pixel counts.

Embodiment 9

Figure 19:
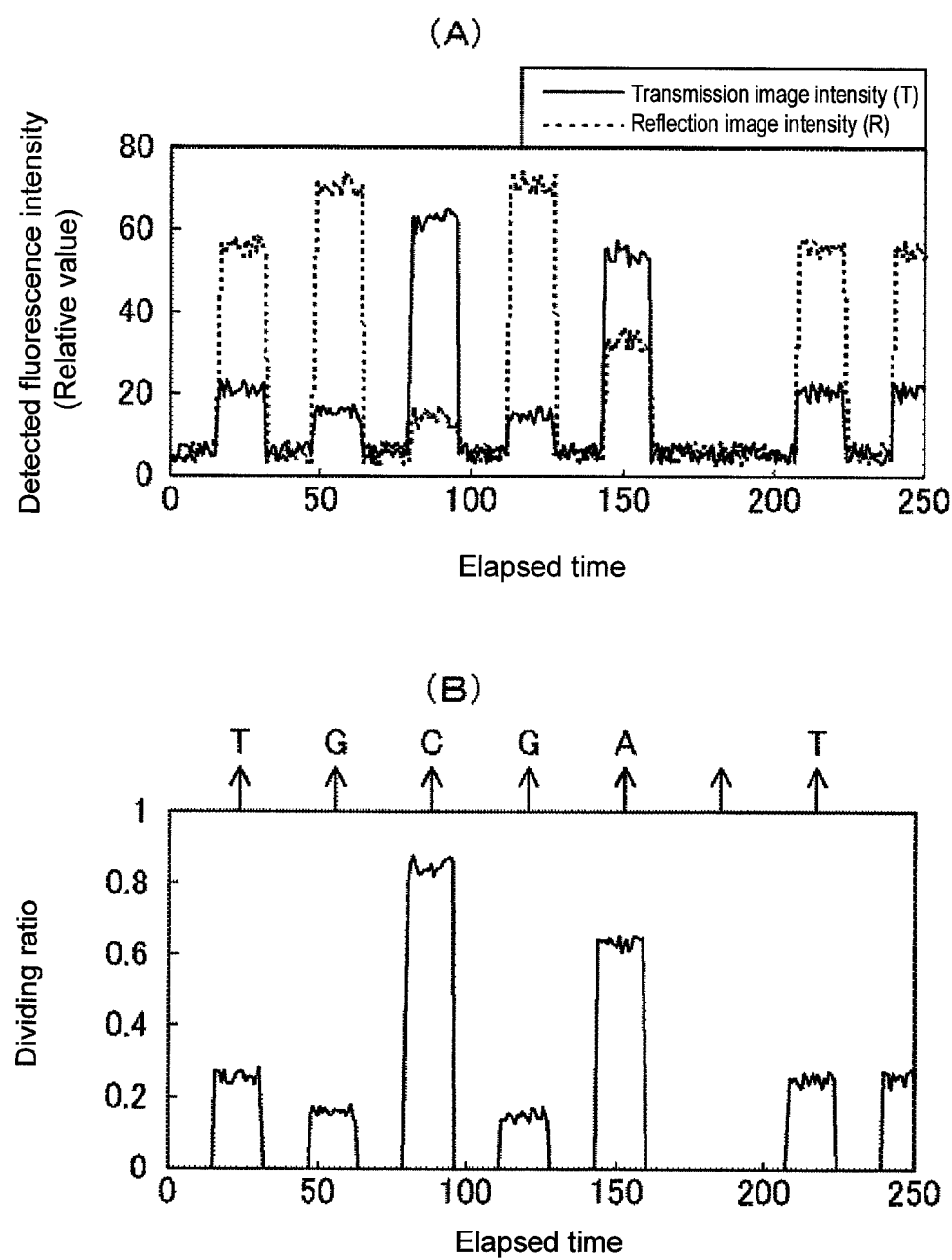
[FIG. 19]

Example measurement of given regions $8ij$ according to the method of Embodiment 1 is described with reference to schematic graphs. Broadly, the steps of (i) elongation reaction→(ii) cleaning→(iii) fluorescence measurement→(iv) fluorescent material removal+3' end recovery→(v) cleaning are repeated. FIG. 19 shows schematic graphs showing (iii) fluorescence measurement and measurement at the time of (v) cleaning. The elapsed time is expressed with the steps of elongation reaction, fluorescent material removal+3' end recovery, and the like being excluded, and is represented by a relative value. FIG. 19(A) shows temporal changes of the transmitted light intensity and the reflected light intensity of fluorescence from the same capture region in the lattice pattern. FIG. 19(B) shows a temporal change of the ratio (dividing ratio) of the transmitted light intensity to the sum of the transmitted light intensity and the reflected light intensity. If a fluorescent material is not captured, it is not worth computing the ratio, and hence the ratio is computed for the case where the sum of the transmitted light intensity and the reflected light intensity is equal to or more than a given value. The ratio is different for each fluorescent material captured in each step, and hence the sequence can be determined as shown in the Figure by the data processing section analyzing timing, detected intensities, dividing ratios, noise widths, and the like. The sequence of all portions of reacting bright spots or molecules can be determined by identifying the lattice point positions in advance or identifying the positions using bright spot positional information after the measurement.

Note that real-time DNA sequencing can also be performed according to a method similar to that of the present embodiment. Because the transmitted light intensity and the reflected light intensity of fluorescence emitted at the time of elongation can be continuously measured at the same time, the base types can be continuously determined on the basis of the ratios thereof, similarly to the above.

Embodiment 10

Another example combination of fluorescent materials is described.

The present embodiment can be applied to fluorescence measurement using excitation energy transfer caused by resonance (so-called FRET). For example, Qdot 525 having a fluorescence wavelength of 525 nm can be used as a donor, and four types of fluorescent materials of Alexa Fluor 546, Alexa Fluor 594, Alexa Fluor 633, and Alexa Fluor 660 can be used as acceptors. These five types of fluorescent materials can be identified and discriminated on the basis of the fluorescence intensity ratios thereof, similarly to the above-mentioned embodiments. In the case of FRET, sample molecules labeled with Qdot are captured at the respective dots (the regions 8$ij$ and the like) of the reaction region described in Embodiment 1 and the like, and are reacted with the four types of fluorescent materials or fluorescently-labeled specific recognition molecules (antibodies, DNA, and the like). The fluorescence intensities are detected and the detected fluorescence intensity ratios are computed by the apparatus described in any of the above-mentioned embodiments, whereby the types of fluorescent materials can be identified. The states of the respective regions include: a dot at which nothing is captured; a dot at which only Qdot is captured; a dot at which Qdot+Alexa Fluor 546 are captured; a dot at which Qdot+Alexa Fluor 594 are captured; a dot at which Qdot+Alexa Fluor 633 are captured; and a dot at which Qdot+Alexa Fluor 660 are captured. Fluorescence is detected from the dots at which Qdot is captured, but the fluorescence intensity ratios thereof are different from one another, and the fluorescence intensities of Qdot are reduced by excitation energy transfer. Accordingly, the combination content can be identified on the basis of the fluorescence intensity ratios.

The present embodiment can be applied to a fluorescence measuring system using a FRET phenomenon. In this case, the number of molecules of the fluorescent materials existing in the respective regions or dots is not one, and hence the present embodiment can be applied to multi-molecule measurement.

Embodiment 11

Description is given of an example in which the transmittance (reflectance) characteristic of the dichroic mirror 32 or 400 is nonlinearly changed in a detection wavelength range. The apparatus configuration is similar to that of FIG. 1, and the fluorescent materials to be used and the laser apparatuses 101$c$ and 101$d$ for fluorescence excitation are the same as those of Embodiment 2.

In general, in order to detect the existence of a fluorescent material at given coordinates (in the present embodiment, coordinates of a metal structure disposed at a lattice point), the brightness of a two-dimensional sensor camera at the given coordinates needs to be more than a predetermined threshold. In the case as in the above-mentioned embodiments where each bright spot derives from a single fluorescent material, in addition to the condition that the brightness exceeds the predetermined threshold, it is necessary to show one-stage quenching (one-stage dissociation, in the case of real-time sequencing) in order to discriminate each bright spot deriving from a single fluorescent material. The brightness (background brightness) of the two-dimensional sensor camera when a fluorescent material does not exist fluctuates spatially and temporally due to shot noise, read-out noise, and the like. Accordingly, in order to prevent a bright spot having the background brightness which happens to exceed the threshold from being discriminated as a fluorescent material, the threshold needs to be set to a sufficiently large value. Meanwhile, a feeble fluorescence material bright spot having the brightness which falls below the threshold can be overlooked. Particularly in the case where the fluorescence intensity is divided by a dichroic mirror, the fluorescence intensity per pixel is smaller, and hence such a feeble fluorescent material bright spot having the brightness which falls below the threshold exists. In the present invention, for example, in some cases, a fluorescent material type having an extremely large transmittance may be discriminated as a fluorescent material bright spot by a transmission-side pixel, and may not be discriminated as a fluorescent material bright spot by a reflection-side pixel because the brightness thereof falls below the threshold. In such a case, the fluorescence intensity ratio can be calculated by acquiring the brightness of the reflection-side pixel corresponding to the transmission-side pixel at which the fluorescent material type is discriminated as the fluorescent material bright spot. Here, the fluorescence intensity ratio is assumed to be given as (transmission-side fluorescence intensity)/(transmission-side fluorescence intensity+reflection-side fluorescence intensity)×100%. Unfortunately, for example, in the case of a fluorescence type having a fluorescence intensity ratio of around 50%, the fluorescence intensity after division halves, and hence a feeble fluorescent material type may not be discriminated as a fluorescent material bright spot by any of the pixels. The feeble fluorescent material type in this case has, for example, low excitation efficiency with the excitation wavelength of this fluorescent material being far from the wavelengths of lasers for excitation.

Figure 20:
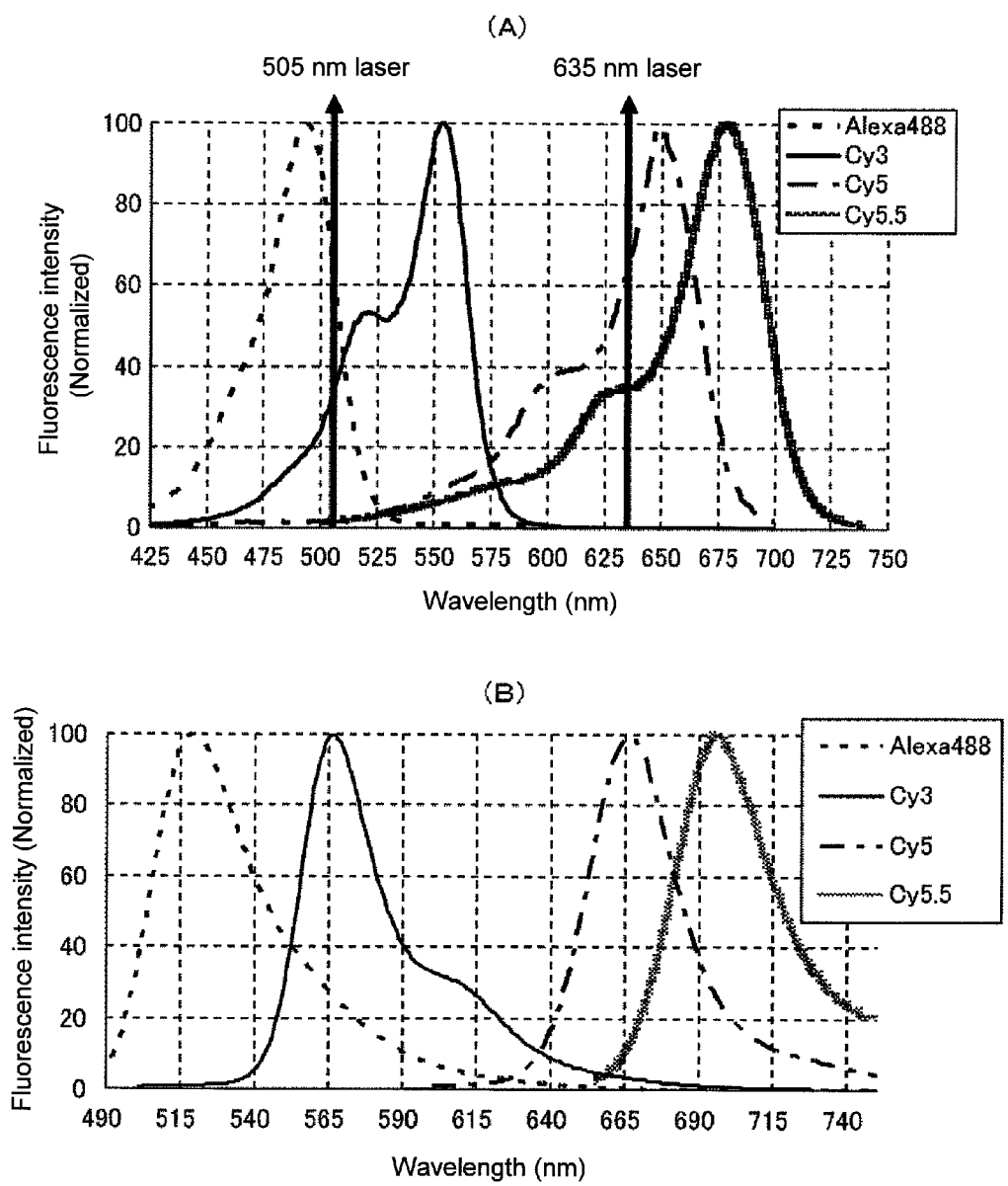
[FIG. 20]

In the present embodiment, a solid-state laser which oscillates a laser beam of 505 nm is used for excitation of Alexa Fluor 488 and Cy3, and a semiconductor laser which oscillates a laser beam of 635 nm is used for excitation of Cy5 and Cy5.5. FIG. 20(A) shows the wavelengths of the lasers for excitation and the excitation spectra of the respective fluorescent materials, and FIG. 20(B) shows the fluorescence spectra thereof. The laser excitation wavelengths of Cy3 and Cy5.5 are far from the laser excitation wavelengths, compared with those of Alexa Fluor 488 and Cy5. Accordingly, the excitation efficiencies of Cy3 and Cy5.5 are lower, so that the fluorescence intensities thereof may be feebler than those of Alexa Fluor 488 and Cy5. Particularly in the case where the fluorescence intensity ratio of Cy3 or Cy5.5 is around 50%, as described above, some of such feeble fluorescent material bright spots may not be discriminated as a bright spot by any of the pixels after division.

Figure 21:
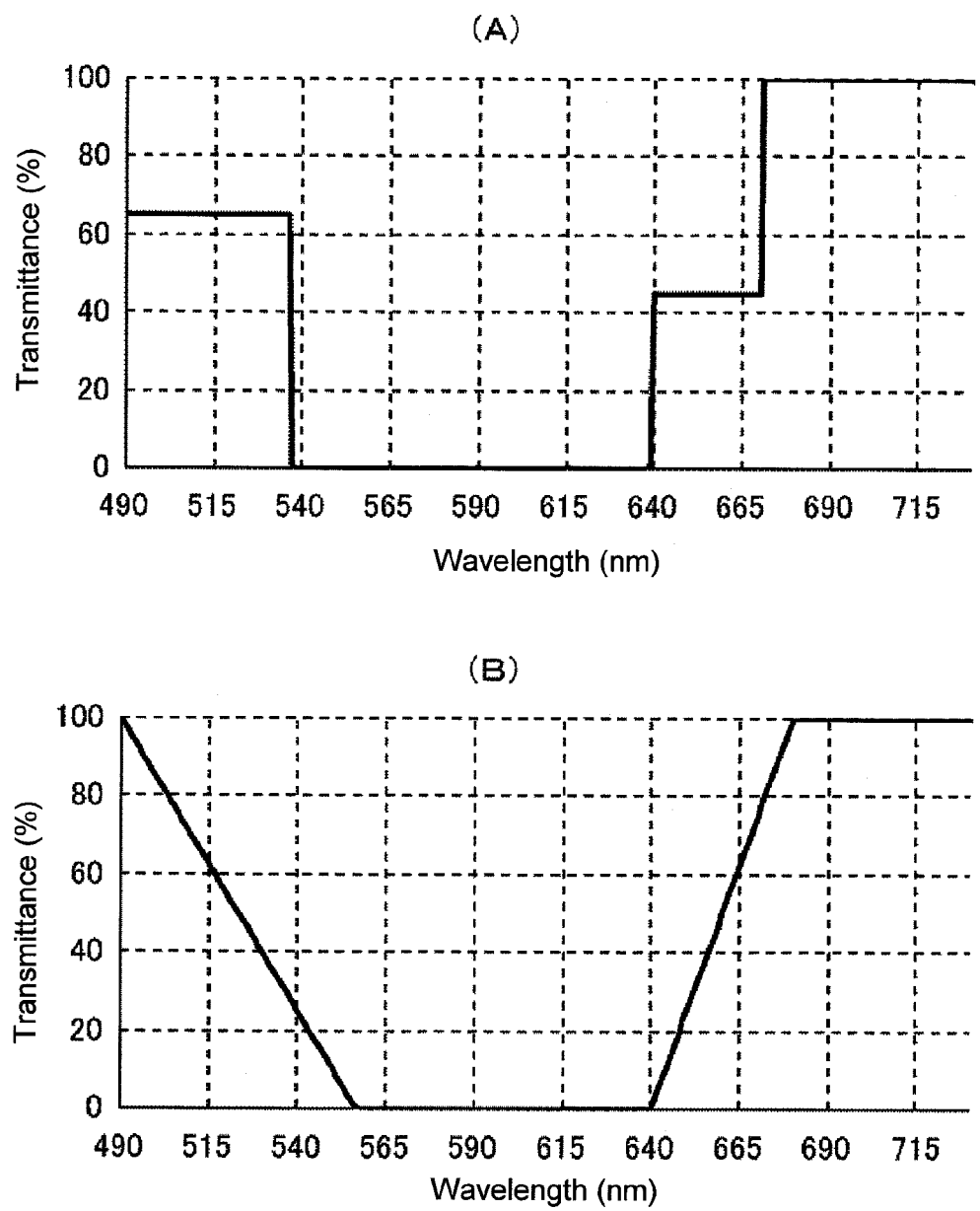
[FIG. 21]

In view of the above, in the present embodiment, the dichroic mirror 32 is designed so as to have a nonlinear transmittance characteristic as shown in FIG. 21(A) or 21(B). Having the nonlinear transmittance characteristic refers to having such a characteristic that includes wavelength ranges with different change ratios of the transmittance to the wavelength. For example, as shown in FIG. 21(A), the transmittance may be changed in a stepwise manner so as to include regions with substantially constant change ratios. Alternatively, as shown in FIG. 21(B), the transmittance may be changed in a slope-like manner so as to mixedly include wavelength ranges with different change ratios. For both the characteristics, the transmittance is 0% in the wavelength range including the fluorescence maximum wavelength (567 nm) of Cy3, and the transmittance is 100% in the wavelength range including the fluorescence maximum wavelength (696 nm) of Cy5.5. As a result, the fluorescent material types having low excitation efficiency, such as Cy3 and Cy5.5, can be preferentially detected on the reflection or transmission side.

Note that, although only the transmittance characteristic of the dichroic mirror 32 is described above, the reflectance characteristic thereof is given as reflectance (%)=(100%−(transmittance (%))), and the sum of the intensities of the reflected light and the transmitted light divided by the dichroic mirror is substantially equal to the original light intensity. As far as the dichroic mirror is concerned, the same applies to the other embodiments.

In the present embodiment, two types of notch filters for laser beam removal (505 nm and 635 to 642 nm) and a bandpass interference filter which transmits a wavelength range to be detected (transmission range: 510 to 730 nm) are used for the filter unit 15.

Figure 22:
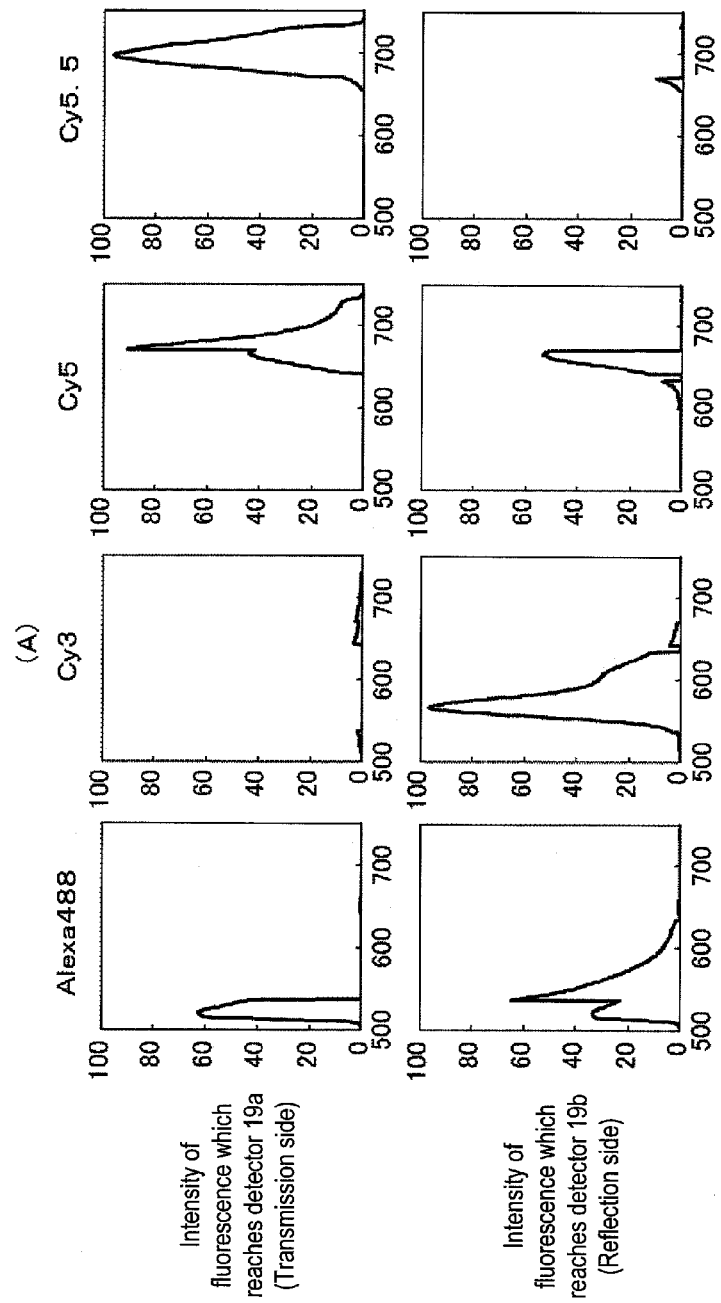
[FIG. 22]

FIG. 22 shows the outline of the fluorescence detection from the respective fluorescent materials. FIG. 22(A) shows the fluorescence spectral components of the respective fluorescent materials which have the fluorescence spectra shown in FIG. 20(B) and reach the two-dimensional sensor cameras 19a and 19b after passing through the filter unit 15, the dichroic mirror 32, and the subsidiary filters 17a and 17b according to the present embodiment. FIG. 22(B) shows computation results of the fluorescence intensity ratios from integral values of the spectra shown in FIG. 22(A), using the fluorescence intensities detected by the transmission-side and reflection-side two-dimensional sensor cameras. The fluorescence intensity ratio of Cy3 is near 0%, and the fluorescence intensity ratio of Cy5.5 is near 100%, so that the feeble fluorescent material molecules can be less likely to be overlooked. In addition, because the characteristics of the dichroic mirror 32 are designed such that the four types of fluorescent materials have different fluorescence intensity ratios, the fluorescent material types can be identified on the basis of the difference in fluorescence intensity ratio. Here, in order to distribute the fluorescence intensity ratios to the four types of fluorescent materials evenly between 0% and 100%, the fluorescence intensity ratio of Alexa Fluor 488 is set to around 33%, and the fluorescence intensity ratio of Cy5 is set to around 66%. Evenly distributing the fluorescence intensity ratios means that, in the case of four-color fluorescent materials, the fluorescence intensity ratios of the respective fluorescent material types are separated from one another by about 33% or more, that is, 100%/((4−1) types)=33%/type. The fluorescence intensity ratio of a fluorescence single-molecule bright spot fluctuates, and hence the identification accuracy of fluorescent material types having fluorescence intensity ratios extremely close to each other decreases. Evenly distributing the fluorescence intensity ratios produces an effect of suppressing such a decrease in identification accuracy of a given fluorescent material type. A similar effect can be obtained even if the fluorescence intensity ratio of Alexa Fluor 488 is set to around 66% and the fluorescence intensity ratio of Cy5 is set to around 33%. In addition, the fluorescence intensity ratio of Cy3 may be set to near 100%, and the fluorescence intensity ratio of Cy5.5 may be set to near 0%. Hereinafter, ideal methods of distributing the fluorescence intensity ratios are described.

In the case where the fluorescence intensity ratios are distributed to n types of fluorescent materials evenly between 0% and 100%, a fluorescence intensity ratio $R_i$(%) of a fluorescent material $F_i$ is set so as to satisfy the following expressions, the fluorescent material $F_i$ having the n−2 $m^{th}$ and n−2m−1$^{th}$ smallest differences between the wavelength of a corresponding laser for excitation and the absorption maximum wavelength.

$$R_i = \frac{100\%}{n-1} \times (n-m-1) \quad \text{Expression 1}$$

or $$R_i = \frac{100\%}{n-1} \times m \quad \text{Expression 2}$$

(where m represents an integer equal to or more than 0, and i represents an integer from 1 to n.)

Note that the corresponding laser for excitation refers to the solid-state laser which oscillates a laser beam of 505 nm in the case of Alexa Fluor 488 and Cy3 and to the semiconductor laser which oscillates a laser beam of 635 nm in the case of Cy5 and Cy5.5. The methods of distributing according to (Expression 1) and (Expression 2) are applied to the examples of Alexa Fluor 488, Cy3, Cy5, and Cy5.5. Because the excitation wavelengths of Cy3 and Cy5.5 are the fourth and third closest to the laser excitation wavelength, n=4 and m=0 are substituted into (Expression 1) and (Expression 2), and up to 100% or 0% is distributed to Cy3 or Cy5.5. In addition, because the excitation wavelengths of Alexa Fluor 488 and Cy5 are the second and first closest thereto, n=4 and k=1 are substituted thereinto, and 33% or 66% is distributed to Alexa Fluor 488 or Cy5. In this way, the fluorescence intensity ratios can be evenly distributed to the four types of fluorescent materials.

A transmittance characteristic D (λ) of the dichroic mirror for giving the fluorescence intensity ratios described above is designed so as to satisfy the following expression for every i from 1 to n.

$$\int F_i(\lambda) D(\lambda) \prod_k f_k(\lambda) d\lambda = R_i / 100\% \quad \text{Expression 3}$$

where $F_i$ (λ) represents the fluorescence spectrum of the fluorescent material $F_i$, and $f_k$ (λ) represents the transmittance characteristics of optical components such as filters through which light emitted from the fluorescent material is transmitted until the light reaches a detector. In actuality, the fluorescence spectrum of the fluorescent material has overlapped portions, and hence it is difficult to design D (λ) so as to satisfy (Expression 3) for every fluorescent material $F_i$. Accordingly, in the present embodiment, D (λ) is designed so as to be as close to the fluorescence intensity ratio $R_i$ as possible. With regard to Alexa Fluor 488, Cy3, Cy5, and Cy5.5, the transmittance characteristics of the filter unit 15 are substituted into $f_k$ (λ), the filter unit 15 including: the two types of notch filters for laser beam removal (505 nm and 635 to 642 nm); and the bandpass interference filter which transmits a wavelength range to be detected (transmission range: 510 to 730 nm). Then, the transmittance characteristic D (λ) of the dichroic mirror is obtained so as to satisfy (Expression 3) as far as possible.

Embodiment 12

In general, at the time of fluorescence measurement using a FRET phenomenon, only light emitted from a donor is detected while FRET is not occurring, and fluorescence from both the donor and acceptors is detected while FRET is occurring. The fluorescence intensity of the donor decreases while FRET is occurring, and the amount of decrease of the fluorescence intensity is given as (donor fluorescence intensity while FRET is not occurring)×(FRET efficiency). Accordingly, whether or not FRET is occurring is determined on the basis of a change in the fluorescence intensity of the donor, whereby the emission of fluorescence from the acceptors can be identified, leading to more accurate detection of the fluorescence intensity.

In the present embodiment, description is given of a method of identifying fluorescent materials, the method using the fluorescence intensity ratios in the case where the fluorescence intensity of Qdot used as the donor is several times higher than those of the acceptors and the FRET efficiency is low. In the case where the fluorescence intensity of Qdot used as the donor is high and the FRET efficiency is low, Qdot has the high fluorescence intensity even while FRET is occurring, and hence fluorescence from acceptor fluorescent materials is hidden by fluorescence from Qdot. As an influence of the fluorescence from Qdot is larger, the fluorescence intensity ratios of the acceptors are affected by the fluorescence intensity ratio of Qdot, and hence the fluorescence intensity ratios of all the acceptors asymptotically approach the fluorescence intensity ratio of Qdot.

Figure 23:
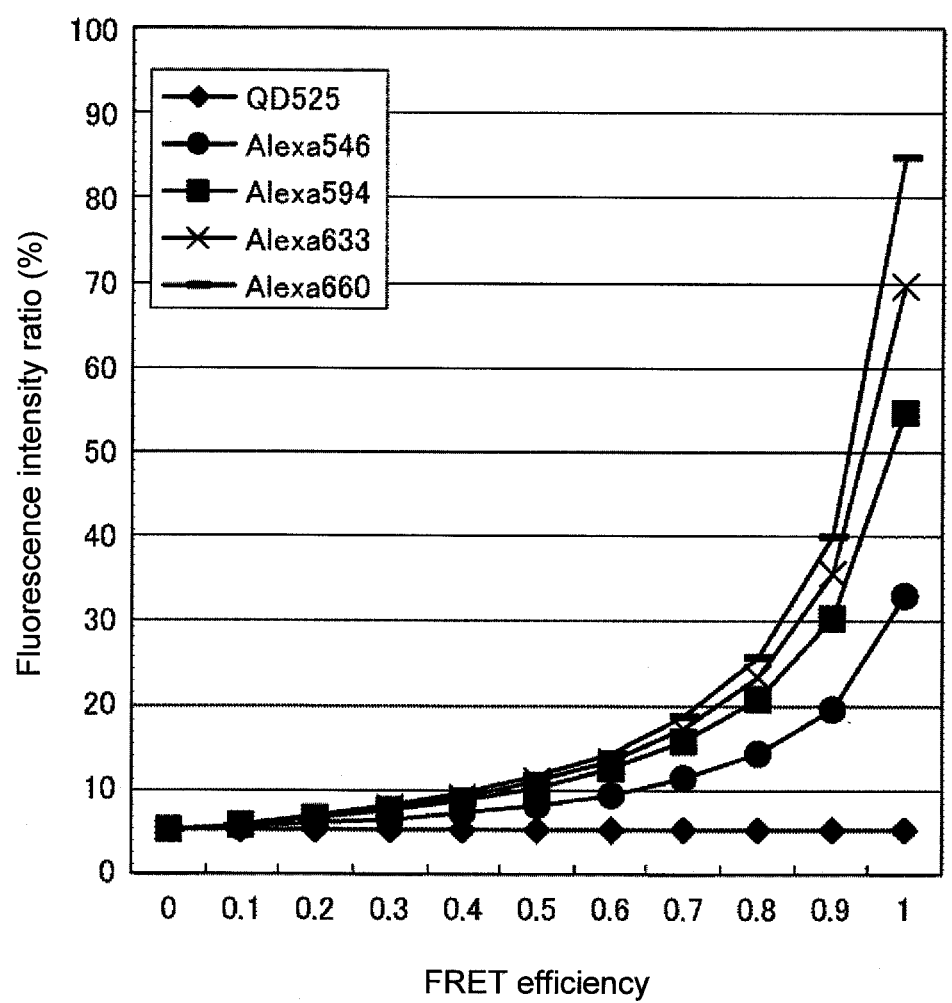
[FIG. 23]

FIG. 23 shows an example relation between the FRET efficiency and the fluorescence intensity ratios of Qdot 525 used as the donor and Alexa Fluor 546, Alexa Fluor 594, Alexa Fluor 633, and Alexa Fluor 660 used as the acceptors. The fluorescence intensities of the four types of Alexa Fluor are normalized to be equal to one another, and the fluorescence intensity of Qdot 525 is set to 10 times those of the four types of Alexa Fluor. With reference to the configuration shown in FIG. 14, a semiconductor laser which oscillates a laser beam of 405 nm is used as the laser apparatus 101e, and no component is provided for the laser apparatus 100. A bandpass filter which transmits light of 510 to 710 nm is used for the filter unit 406, and a dichroic mirror having the characteristic shown in FIG. 15(B) is used as the dichroic mirror 400. As shown in FIG. 23, under the condition that the fluorescence intensity of Qdot 525 is 10 times higher than those of the four types of Alexa Fluor, the fluorescence intensity ratios of all the four types of Alexa Fluor asymptotically approach the fluorescence intensity ratio of Qdot 525 to 5%, as the FRET efficiency is lower. In such a low FRET efficiency region, it is difficult to identify the types of Alexa Fluor on the basis of the difference in fluorescence intensity ratio.

FIG. 24(A) shows a configuration of a detecting system according to the present embodiment. Even in the case where the fluorescence intensity of the donor is high and the FRET efficiency is low, the present embodiment can facilitate the acceptor identification based on the fluorescence intensity ratios. A dichroic mirror 501 having a transmittance characteristic as shown in FIG. 24(B) is disposed between the filter unit 406 and the dichroic mirror 400, and only fluorescent components of Qdot 525 are separated by the dichroic mirror 501. Images of bright spots deriving from Qdot are formed on a two-dimensional sensor camera 503 via an imaging lens 502. A long-pass filter which transmits light of 488 nm or more is used for the filter unit 406, and a dichroic mirror having the characteristic shown in FIG. 15(B) is used as the dichroic mirror 400. Because the light emission components of Qdot 525 are separated by the dichroic mirror 501, an effect of preventing the fluorescence from Qdot 525 from overlapping with Alexa Fluor fluorescence signals can be obtained. Because the fluorescence intensity of Qdot 525 is higher than those of the four types of Alexa Fluor, the sensitivity and price of the two-dimensional sensor camera 503 may be lower than those of the two-dimensional sensor camera 408. Qdot 525 may be randomly fixed, but if Qdot 525 is fixed in a lattice pattern as described in Embodiment 1, the same bright spot A can be easily found as shown in schematic views of detected images of FIG. 24(A).

Figure 25:
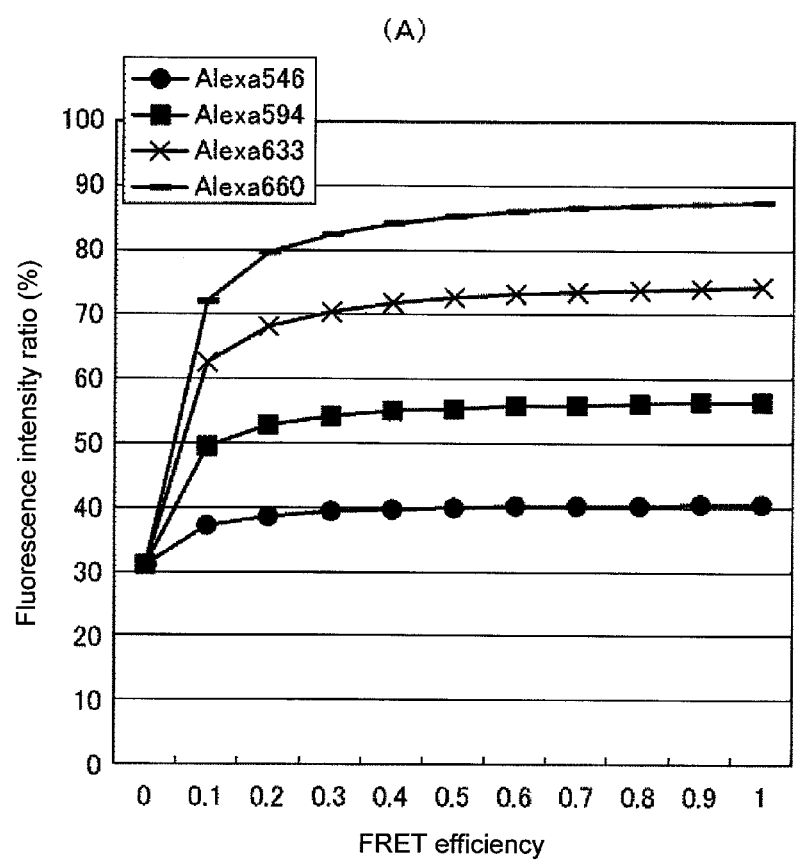
[FIG. 25]

FIG. 25(A) shows an expected relation between the FRET efficiency and the fluorescence intensity ratios at the time of FRET observation using the configuration of FIG. 24(A). When the FRET efficiency is 0, the fluorescence intensities of the four types of Alexa Fluor are 0, and hence the fluorescence intensity ratios thereof are equal to that of Qdot 525. When the FRET efficiency is other than 0, almost no asymptotic approach of the fluorescence intensity ratios of the four types of Alexa Fluor to that of Qdot is observed. In addition, FIG. 25(B) shows the fluorescence intensity ratios when the FRET efficiency is 0.5. The fluorescence intensity ratios of the four types of Alexa are sufficiently different from one another, and hence the fluorescent material types can be identified on the basis of the difference in fluorescence intensity ratio. Note that Qdot 525 and the above-mentioned four types of Alexa Fluor are used in the present embodiment, but the combination of different fluorescent materials may be used.

In addition, in the present embodiment, the fluorescence intensity of Qdot 525 is detected independently by the separate camera. Depending on the characteristics of the dichroic mirror 501, part of the fluorescence from Qdot 525 may be detected by the two-dimensional sensor camera 408. In this case, the amount of leakage thereof to the two-dimensional sensor camera 408 is calculated for correction on the basis of data in the two-dimensional sensor camera 503. As a result, the fluorescent material types can be identified on the basis of more accurate difference in fluorescence intensity ratio.

Embodiment 13

In the present embodiment, the transmittance characteristic of the dichroic mirror 400 (FIG. 24(A)) according to Embodiment 12 is nonlinearly changed in a detection wavelength range similarly to Embodiment 11, and a fluorescent material having low excitation efficiency is detected at a high fluorescence intensity on the transmission side or the reflection side. Accordingly, a feeble fluorescent material caused by the low excitation efficiency can be less likely to be overlooked. Particularly in the case where the FRET efficiency is low, the fluorescence intensities of the acceptors decrease, and hence an effect produced by the present embodiment is enhanced.

The apparatus configuration is the same as that of Embodiment 12. With regard to fluorescent materials for FRET observation, Qdot 525 is used as the donor, and Alexa Fluor 546, Alexa Fluor 594, Alexa Fluor 635, and Alexa Fluor 660 are used as the acceptors.

FIG. 26(A) shows a transmittance characteristic of the dichroic mirror 400 designed according to the method of Embodiment 11. The excitation efficiency decreases with increasing distance from the fluorescence wavelength of Qdot 525. That is, Alexa Fluor 546, Alexa Fluor 594, Alexa Fluor 635, and Alexa Fluor 660 are expected to be lower in fluorescence intensity in the stated order. In view of this, according to this fluorescence intensity order, ideal fluorescence intensity ratios of the respective fluorescent materials are calculated using (Expression 1) and (Expression 2), and the transmittance characteristic of the dichroic mirror 400 is designed so as to satisfy (Expression 3) as far as possible. Note that the transmittance characteristic is changed in a stepwise manner in FIG. 26(A), and alternatively, the transmittance may be changed in a slope-like manner as shown in FIG. 21(B). FIG. 26(B) shows changes of the fluorescence intensity ratios to the FRET efficiency. FIG. 26(C) shows the fluorescence intensity ratios when the FRET efficiency is 0.5. As is apparent from the two figures, with the aid of the dichroic mirror of the present embodiment, Alexa Fluor 660 and Alexa Fluor 635 having low excitation efficiency can be efficiently detected respectively on the transmission side and the reflection side. Further, the fluorescence intensity ratios are distributed to the four types of Alexa Fluor substantially evenly between 20% and 90%.

The dichroic mirror described above has an effect of making a feeble fluorescent material bright spot less likely to be overlooked and suppressing the fluorescent material identification accuracy from decreasing due to fluctuations in fluorescence intensity ratio, mainly at the time of FRET observation with low FRET efficiency.

Embodiment 14

FIG. 27 shows an example in which FRET observation is performed by one two-dimensional sensor camera. The fluorescence from Qdot used as the donor is separated by the dichroic mirror 501 as described in Embodiment 12, and the fluorescence from each acceptor is separated by the dichroic mirror 400 having the transmittance characteristic as described in Embodiments 12 and 13. Images of the fluorescence separated into three optical paths are formed on the two-dimensional sensor camera 408 via the imaging lens 407. As shown in a schematic view of detected images of FIG. 27, a chip of the two-dimensional sensor camera 408 is divided into three, and a fluorescent image of only Qdot, a transmission-side acceptor fluorescent image, and a reflection-side acceptor fluorescent image are given thereon in the stated order from the left. Similarly to Embodiments 12 and 13, the fluorescence intensity ratios are calculated on the basis of the transmission-side and reflection-side fluorescence intensities with respect to the fluorescent images of the same bright spots of the acceptors, whereby the acceptor fluorescent materials can be identified. The present embodiment produces an effect of reducing the apparatus costs by detecting the three types of fluorescent images using one two-dimensional sensor camera.

Note that a neutral density filter may be provided between the mirror 401 and the lens 407. If the fluorescence intensity of Qdot is excessively high, the fluorescence intensity thereof is reduced by the neutral density filter, whereby the three types of fluorescent images can be adjusted to have an appropriate brightnesses level, leading to easier image measurement.

Embodiment 15

In the present embodiment, description is given of a method of separating fluorescence from the donor and the acceptors by one dichroic mirror and detecting the separated light fluxes on the transmission side and the reflection side by the same two-dimensional sensor camera, at the time of FRET observation. With regard to reagents for FRET observation, similarly to Embodiment 13, Qdot 525 is used as the donor, and Alexa Fluor 546, Alexa Fluor 594, Alexa Fluor 635, and Alexa Fluor 660 are used as the acceptors. The configuration shown in FIG. 1 or FIG. 14 is used for the detecting system. A semiconductor laser which oscillates a laser beam of 405 nm is used as the laser apparatus 101b or 101e for donor excitation. The characteristic of the dichroic mirror 32 or 400 is as shown in FIG. 15(B).

A long-pass filter (short-wavelength cut filter) having a rise between the fluorescence maximum wavelengths of Qdot 525 and Alexa Fluor 546 as shown in FIG. 28 is used for the filter unit 15 or 406. Part of the fluorescence from Qdot 525 is cut by the long-pass filter, whereby the fluorescence intensity thereof is reduced. This prevents fluorescence signals of Qdot 525 used as the donor from becoming more influential. Particularly at low FRET efficiency, the fluorescence intensity ratios of the acceptors can be suppressed from asymptotically approaching the fluorescence intensity ratio of the donor. Qdot 525 used as the donor is assumed to have a fluorescence intensity 10 times higher than those of the four types of Alexa Fluor used as the acceptors. In this case, as shown in FIG. 23, the fluorescence intensity ratios of the four types of Alexa Fluor rapidly asymptotically approach the value of Qdot 525, as the FRET efficiency is lower. In contrast, in the case where the fluorescence intensity of Qdot 525 is reduced to 1/10 by the long-pass filter as shown in FIG. 28(A), the speed of such asymptotic approach can be relatively slowed down as shown in FIG. 28(B), and hence enhancement in fluorescent material identification accuracy can be expected. A change in the fluorescence intensity of the donor is necessary to confirm FRET occurrence. Accordingly, it is appropriate to reduce the fluorescence intensity of the donor to 0.5 times to 5 times those of the acceptors such that the fluorescence intensity of the donor and a decrease in the fluorescence intensity thereof during FRET occurrence can be sufficiently detected and a saturation charge amount of the two-dimensional sensor camera is not exceeded. For example, if the fluorescence intensity of the donor is 10 times those of the acceptors, it is appropriate to design the long-pass filter such that the fluorescence intensity of the donor is reduced to 1/2 to 1/20. Instead of FIG. 28(A), as shown in FIG. 29(A), the long-pass filter may have a constant transmittance characteristic in the fluorescence wavelength range of Qdot 525 used as the donor. In this case, an effect of suppressing a change in transmitted fluorescence intensity caused by a wavelength shift of Qdot 525 can be obtained. Alternatively, such a gentle slope as shown in FIG. 29(B) may be adopted. In this case, an effect of facilitating the production of the filter can be obtained in addition to a similar effect to that of FIG. 29(A). Note that a notch filter and a bandpass filter may be used instead of the long-pass filter. The dichroic mirror 32 or 400 may have the transmittance (reflectance) characteristic which is nonlinearly changed according to the method described in Embodiment 11, instead of the characteristic shown in FIG. 15(B).

Figure 30:
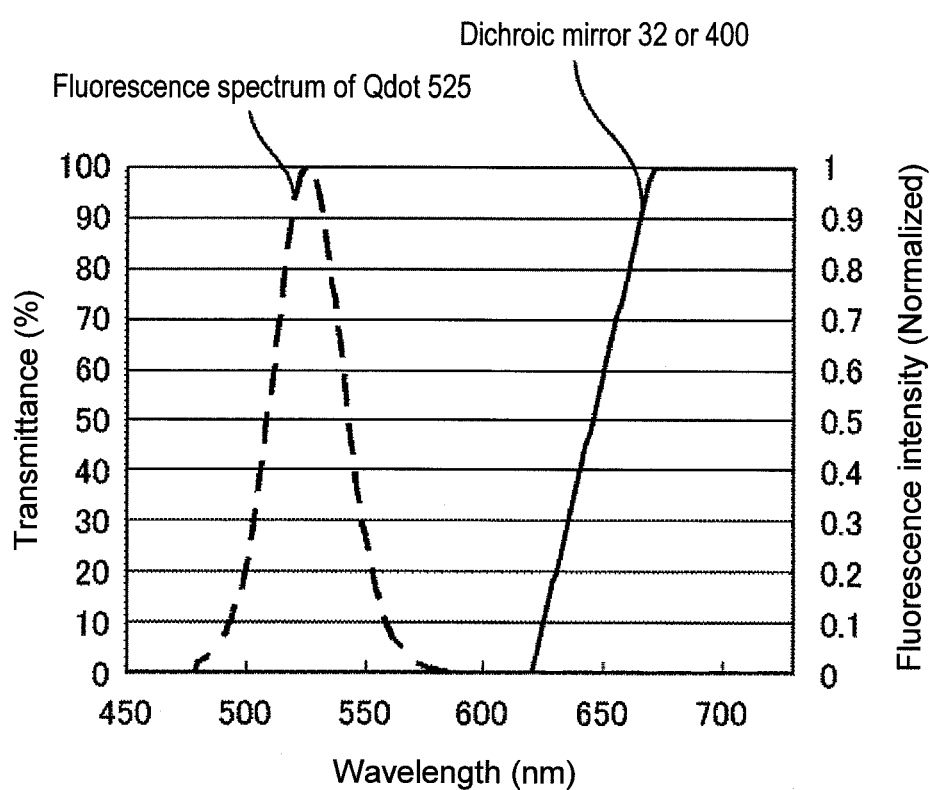
[FIG. 30]

Alternatively, the dichroic mirror 32 or 400 may have such a characteristic as shown in FIG. 30. That is, the transmittance of the fluorescence wavelength range of the donor (Qdot 525) may be set to substantially 0% (the reflectance is substantially 100%), and the transmittance may be increased substantially linearly from the maximum wavelength of the acceptor fluorescent material (Alexa Fluor 546) having the shortest wavelength to the maximum wavelength of the acceptor fluorescent material (Alexa Fluor 660) having the longest wavelength. At this time, almost all fluorescent components of Qdot 525 are detected as reflection-side images, and hence the fluorescence intensity ratio thereof is substantially 0. Because the fluorescence intensity ratio of Qdot 525 is substantially 0, the fluorescence intensity ratios can be distributed to the four types of Alexa Fluor substantially evenly between 0% and 100%, and hence enhancement in identification accuracy of the acceptor fluorescent material types can be expected. Note that the transmittance of the dichroic mirror 32 or 400 shown in FIG. 30 may be nonlinearly changed as described in Embodiment 11 instead of being linearly changed.

In addition, with regard to the reagents for FRET observation, various combinations other than the above may be adopted. For example, Qdot 565 may be used as the donor, and Alexa Fluor 635, Alexa Fluor 660, Alexa Fluor 700, and Alexa Fluor 750 may be used as the acceptors. FIG. 31(A) shows the fluorescence spectra of these reagents, FIG. 31(B) shows the transmittance characteristic of the long-pass filter (bandpass filter) in the case of these reagents, and FIG. 31(C) shows the transmittance characteristic of the dichroic mirror in the case of these reagents. Also in this case, similarly to the above, because the fluorescence intensity ratio of Qdot 565 is substantially 0, the fluorescence intensity ratios can be distributed to the four types of Alexa Fluor fluorescent materials substantially evenly between 0% and 100%, and hence enhancement in identification accuracy of the acceptor fluorescent material types can be expected.

| Reference Signs List | |
|---|---|
| 5, 104b, 104e, 401, 402, 403 | mirror |
| 7 | prism |
| 8, 60 | substrate |
| 8a, 60a | reaction region |
| 8ij, 60ij | region for capturing DNA |
| 9, 204 | flow chamber |
| 10 | waste liquid tube |
| 11 | waste liquid container |
| 12 | reagent inlet |
| 13 | fluorescence |
| 14 | light collecting lens (objective lens) |
| 15, 406 | filter unit |
| 16 | lens barrel for transmitted light observation |
| 17a, 17b, 17c, 17d, 17e, 404, 405 | subsidiary filter |
| 18a, 18b, 18c, 18d, 18e, 407, 502 | imaging lens |
| 19a, 19b, 19c, 19d, 19e, 408, 503 | two-dimensional sensor camera |
| 20a, 20b, 409 | two-dimensional sensor camera controller |
| 21 | control PC |
| 22, 24 | monitor |
| 23 | TV camera |
| 25 | dispensing unit |
| 26 | dispensing nozzle |
| 27 | reagent storing unit |
| 27a | sample solution container |
| 27b, 27c, 27d, 27e | dNTP derivative solution container |
| 27f | cleaning liquid container |
| 28 | chip box |
| 29 | automatic focusing apparatus |
| 30, 31, 61, 62, 63 | positioning marker |
| 32, 103, 104a, 300, 301, 400, 501 | dichroic mirror |
| 60b | mask |
| 100, 101a, 101b, 101c, 101d, 101e | laser apparatus |
| 102a, 102b, 102c, 102d, 102e | λ/4 wave plate |
| 200 | measurement substrate |
| 201 | PDMS resin |
| 202 | hollow |
| 203 | holder |
| 205 | substrate holding tool |
| 206 | through-hole |
| 207 | opening |
| 208 | flow path |
| 209 | X-Y stage |
| 210 | prism holder |
| dx, dy | interval between regions 8ij |

The invention claimed is:

1. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:
   a substrate including a plurality of regions in which molecules are to be captured, the regions being disposed at lattice point positions of a lattice structure;
   a light source for light excitation;
   a irradiation optical system;
   a fluorescence collecting system;
   a dividing section which divides collected light at ratios substantially different for each wavelength in a specified wavelength range;
   an imaging optical system which forms an image of each divided light flux on a detector;
   the detector including a plurality of pixels for detecting the formed image of each divided light flux; and
   a data processing section which determines a fluorescent material type on a basis of an intensity ratio of the detected light flux.

2. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:
   a substrate including a plurality of regions in which molecules are to be captured, the regions being disposed at lattice point positions of a lattice structure;
   a light source for light excitation;
   a irradiation optical system;
   a fluorescence collecting system;
   a dividing section which divides fluorescence of a plurality of fluorescent materials at ratios different for each specified wavelength range; and
   a detector including pixels for detecting the fluorescence divided at the different ratios.

3. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:
   a substrate including a plurality of regions in which molecules are to be captured or a substrate on which molecules are captured;
   a light source for light excitation;
   a irradiation optical system;
   a fluorescence collecting system;
   a dividing section which divides fluorescence of a plurality of fluorescent materials at ratios different for each specified wavelength range; and
   a detector including pixels for detecting the fluorescence divided at the different ratios.

4. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:
   a substrate on which molecules are to be captured or a substrate on which molecules are captured;
   a light source for light excitation;
   a irradiation optical system;
   a fluorescence collecting system;
   a dividing section which divides collected light at ratios substantially different for each wavelength in a specified wavelength range; and
   a detector including pixels for detecting the light fluxes divided at the different ratios.

5. The fluorescence detecting apparatus according to any of claims 1 to 4, wherein:

a plurality of fluorescent materials exist on the substrate;

the fluorescent materials generate fluorescence different from one another;

intensities of the fluorescence are detected by one or two detectors including a plurality of pixels; and a fluorescence intensity ratio of one of the fluorescent materials is different from fluorescence intensity ratios of the other fluorescent materials.

6. The fluorescence detecting apparatus according to claim 1 or 2, further comprising a fine metal structure provided at each of the lattice point positions of the lattice structure.

7. The fluorescence detecting apparatus according to claim 1 or 2, further comprising:

a fine opening formed at each of the lattice point positions of the lattice structure; and a substrate made of an optically opaque thin film.

8. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:

a substrate including a plurality of regions in which molecules are to be captured or a substrate on which molecules are captured;

a light source for light excitation;

a irradiation optical system;

a fluorescence collecting system;

N ($\geq 1$) detectors including a plurality of pixels for detecting collected light at ratios substantially different for each wavelength in a specified wavelength range; and a data processing section which identifies K ($>N$) types of fluorescent materials on a basis of the ratios.

9. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:

a substrate including a plurality of regions in which molecules are to be captured or a substrate on which molecules are captured;

a light source for light excitation;

a irradiation optical system;

a fluorescence collecting system;

a dividing section which divides fluorescence of four or more types of fluorescent materials at ratios different for each fluorescence maximum wavelength range; and a detector including pixels for detecting the light fluxes divided at the different ratios.

10. A fluorescence detecting apparatus which radiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus comprising:

a substrate including a plurality of regions in which molecules are to be captured or a substrate on which molecules are captured;

a light source for light excitation;

a irradiation optical system;

a fluorescence collecting system;

a dividing section which divides fluorescence of four or more types of fluorescent materials at ratios different for each fluorescence maximum wavelength range; and a single detector including pixels for detecting the light fluxes divided at the different ratios.

11. The fluorescence detecting apparatus according to any of claims 1 to 4, wherein:

the substrate is substantially transparent; and the irradiation optical system serves for total-reflection illumination.

12. The fluorescence detecting apparatus according to any of claims 8 to 10, wherein:

the substrate is substantially transparent; and the irradiation optical system serves for total-reflection illumination.

13. The fluorescence detecting apparatus according to any of claims 1 to 4 and 8 to 10, wherein:

the biologically relevant molecules include oligonucleotides; and the separating section has such a characteristic that makes a transmittance substantially 0% and substantially 100% or substantially 100% and substantially 0% for fluorescence maximum wavelengths of a first fluorescent material type and a second fluorescent material type, the first fluorescent material type having the largest difference between a wavelength of excitation light and an absorption maximum wavelength of the first fluorescent material type, the second fluorescent material type having the second largest difference between the wavelength of the excitation light and an absorption maximum wavelength of the second fluorescent material type.

14. The fluorescence detecting apparatus according to any of claims 1 to 4 and 8 to 10, wherein:

the fluorescence is emitted from each of a plurality of fluorescent materials; and one of the plurality of fluorescent materials is a donor excited by the light source for light excitation, and the other fluorescent materials are acceptor fluorescent materials excited by energy transfer from the donor.

15. The fluorescence detecting apparatus according to claim 14, further comprising a dichroic mirror which separates fluorescence from the donor into an optical path substantially different from optical paths of fluorescence from the acceptors, wherein the fluorescence from the acceptors is divided by the dividing section at ratios different for each different fluorescence maximum wavelength range.

16. A fluorescence detecting apparatus which irradiates light for fluorescence measurement to a substrate on which biologically relevant molecules are captured, collects fluorescence generated therefrom, and performs fluorescence detection, the fluorescence detecting apparatus comprising:

a dividing section which divides collected light at ratios substantially different for each wavelength in a specified wavelength range;

a detector for detecting each divided light flux; and a data processing section which determines a fluorescent material type on a basis of an intensity ratio of the detected light flux.

17. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus being configured to:

divide fluorescence from each region in which molecules are captured or fluorescence from each captured fluorescent molecule at ratios substantially different for each wavelength in a specified wavelength range;

detect each divided light flux using 25 pixels or less per bright spot; and determine a fluorescent material type on a basis of an intensity ratio of the detected light flux.

18. A fluorescence detecting apparatus which irradiates light for fluorescence measurement to a substrate on which biologically relevant molecules are captured, collects fluorescence generated therefrom, forms an image of the collected fluorescence on a two-dimensional detector, and causes the two-dimensional detector to perform fluorescence detection, the fluorescence detecting apparatus being configured to:

divide fluorescence from each region in which molecules are captured or fluorescence from each captured fluorescent molecule at ratios substantially different for each wavelength in a specified wavelength range;

form an image of each divided light flux within 9 pixels or less per bright spot and detect the formed image; and determine a fluorescent material type on a basis of an intensity ratio of the detected light flux.

19. A fluorescence detecting apparatus according to any of claims 16 to 18, wherein the biologically relevant materials include oligonucleotides.

* * * * *